US012670983B2

(12) United States Patent
Tachibana

(10) Patent No.: US 12,670,983 B2
(45) Date of Patent: Jun. 30, 2026

(54) MACHINE LEARNING MODEL CREATION SUPPORT APPARATUS, METHOD OF OPERATING MACHINE LEARNING MODEL CREATION SUPPORT APPARATUS, AND PROGRAM FOR OPERATING MACHINE LEARNING MODEL CREATION SUPPORT APPARATUS

(71) Applicant: FUJIFILM Corporation, Tokyo (JP)

(72) Inventor: Atsushi Tachibana, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 314 days.

(21) Appl. No.: 18/472,268

(22) Filed: Sep. 22, 2023

(65) Prior Publication Data

US 2024/0013894 A1 Jan. 11, 2024

Related U.S. Application Data

(63) Continuation of application No. PCT/JP2022/008070, filed on Feb. 25, 2022.

(30) Foreign Application Priority Data

Mar. 30, 2021 (JP) ................................. 2021-057322

(51) Int. Cl.
  *G16H 30/40* (2018.01)
  *G06V 10/764* (2022.01)
    (Continued)

(52) U.S. Cl.
  CPC ........... *G16H 30/40* (2018.01); *G06V 10/764* (2022.01); *G06V 20/70* (2022.01); *G06V 40/103* (2022.01)

(58) Field of Classification Search
  CPC . G06T 2207/20081; G06T 2207/20084; G06T 7/0012; G06T 2207/30024;
    (Continued)

(56) References Cited

U.S. PATENT DOCUMENTS

| | | |
|---|---|---|
| 11,062,800 B2 | 7/2021 | Lee et al. |
| 11,335,455 B2 | 5/2022 | Lee et al. |
| | (Continued) | |

FOREIGN PATENT DOCUMENTS

| | | |
|---|---|---|
| JP | 2019096006 | 6/2019 |
| JP | 2020091543 | 6/2020 |
| | (Continued) | |

OTHER PUBLICATIONS

Le Zhang, Ryutaro Tanno, Moucheng Xu, Yawen Huang, Kevin Bronik, Chen Jin, Joseph Jacob, Yefeng Zheng, Ling Shao, Olga Ciccarelli, Frederik Barkhof, Daniel C. Alexander, Learning from multiple annotators for medical image segmentation, Pattern Recognition, (Year: 2023).*

(Continued)

*Primary Examiner* — Alex Kok S Liew
(74) *Attorney, Agent, or Firm* — JCIPRNET

(57) ABSTRACT

A machine learning model creation support apparatus including a processor, in which the processor acquires a plurality of pieces of annotation information generated by a plurality of annotators assigning a plurality of labels according to a plurality of classes to a region of the same medical image, derives, for each of the classes, commonality data indicating commonality in how the labels are assigned by the plurality of annotators for the plurality of pieces of annotation information, and generates confirmed annotation information used as correct answer data of a machine learning model based on the commonality data and a preset confirmation condition.

11 Claims, 19 Drawing Sheets

(51) Int. Cl.
  G06V 20/70 (2022.01)
  G06V 40/10 (2022.01)

(58) Field of Classification Search
  CPC ............. G06T 2207/30096; G06T 7/11; G06T
    2207/10056; G06T 2207/20021; G06T
    2207/10081; G06T 2207/30004; G06T
    2207/30068; G06T 2207/10088; G06T
    2207/10104; G06T 7/0014; G06T 7/174;
    G06T 7/194; G06T 2207/20104; G06T
    7/0016; G06T 7/70; G06T 2207/10024;
    G06T 7/0002; G06T 7/12; G06T 2200/04;
    G06T 2207/30168; G06T 2207/20076;
    G06T 7/62; G06T 2207/20016; G06T
    7/187; G06T 19/00; G06T 2207/10016;
    G06T 2207/30204; G06T 2219/004;
    G06T 2207/10072; G06T 5/50; G06T
    7/10; G06T 11/20; G06T 11/60; G06T
    2200/24; G06T 2207/30061; G06T
    2210/12; G06T 5/60; G06T 5/73; G06T
    2207/10012; G06T 2207/10064; G06T
    2207/10116; G06T 2207/20101; G06T
    2207/20221; G06T 2207/30016; G06T
    2207/30072; G06T 7/136; G06T 7/149
  See application file for complete search history.

(56) References Cited

U.S. PATENT DOCUMENTS

| | | | |
|---|---|---|---|
| 12,217,853 | B2 | 2/2025 | Lee et al. |
| 2018/0276815 | A1* | 9/2018 | Xu ........................... G06N 3/09 |
| 2019/0156157 | A1 | 5/2019 | Saito et al. |
| 2020/0167671 | A1 | 5/2020 | Okada et al. |
| 2020/0175377 | A1 | 6/2020 | Iio et al. |
| 2021/0272284 | A1 | 9/2021 | Kamiyama |
| 2021/0358585 | A1* | 11/2021 | Wu ........................ G16H 10/60 |
| 2025/0132021 | A1 | 4/2025 | Lee et al. |

FOREIGN PATENT DOCUMENTS

| | | |
|---|---|---|
| JP | 2021502652 | 1/2021 |
| JP | 2021039748 | 3/2021 |
| WO | 2019003485 | 1/2019 |
| WO | 2020194662 | 10/2020 |

OTHER PUBLICATIONS

"International Search Report (Form PCT/ISA/210) of PCT/JP2022/008070", mailed on May 17, 2022, with English translation thereof, pp. 1-5.
"Written Opinion of the International Searching Authority (Form PCT/ISA/237) of PCT/JP2022/008070", mailed on May 17, 2022, with English translation thereof, pp. 1-8.
"Notice of Reasons for Refusal of Japan Counterpart Application", issued on Aug. 5, 2025, with English translation thereof, p. 1-p. 9.

* cited by examiner

LABEL: LIVER

LABEL: LIVER TUMOR BLEEDING

LABEL: LIVER TUMOR

Figure 9:
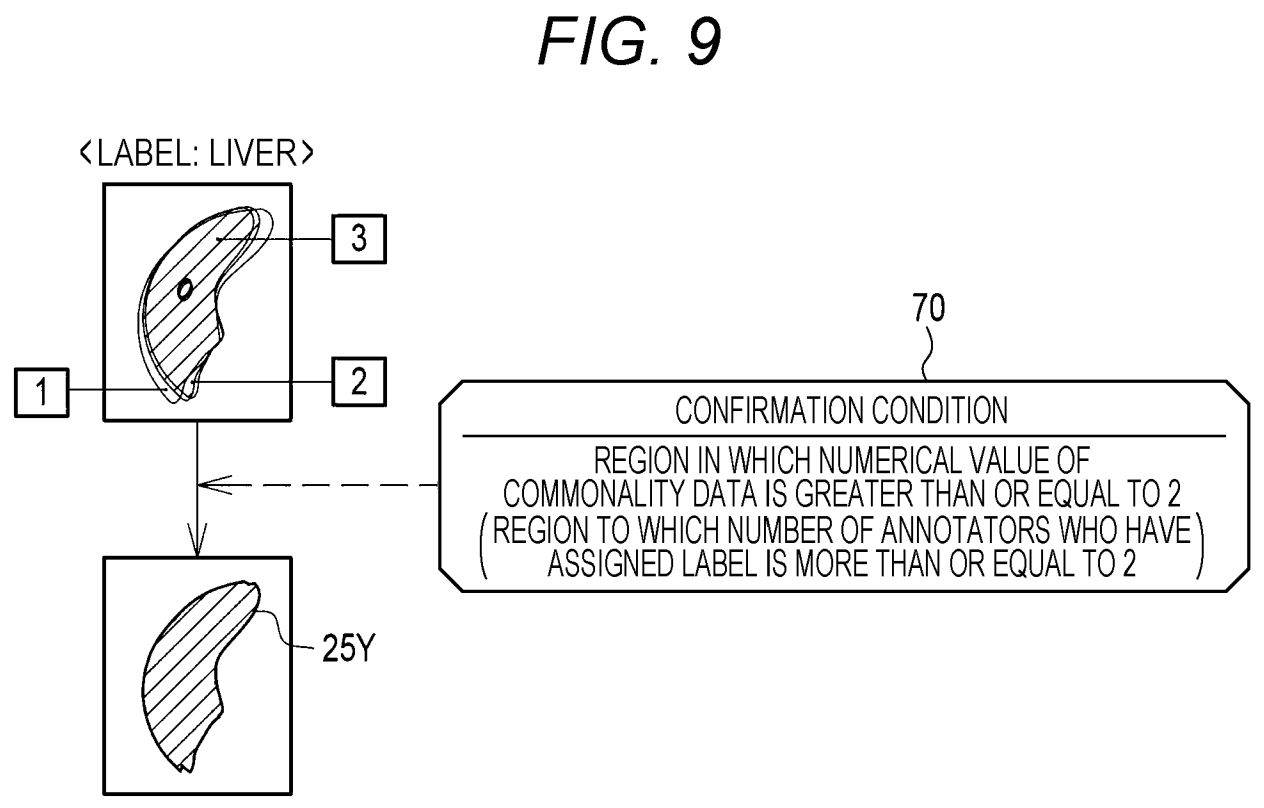

〈LABEL: LIVER〉

1　2　3

70

CONFIRMATION CONDITION

REGION IN WHICH NUMERICAL VALUE OF
COMMONALITY DATA IS GREATER THAN OR EQUAL TO 2
( REGION TO WHICH NUMBER OF ANNOTATORS WHO HAVE
ASSIGNED LABEL IS MORE THAN OR EQUAL TO 2 )

25Y

CONFIRMATION CONDITION

REGION IN WHICH RATIO OF ANNOTATORS WHO HAVE ASSIGNED LABEL IS MORE THAN OR EQUAL TO 90%

76

<CLASS: LIVER>

75

| POSITION COORDINATES | RATIO OF ANNOTATORS WHO HAVE ASSIGNED LABEL |
|---|---|
| ... | ... |
| (10,10,10) | 100% |
| (11,10,10) | 90% |
| (12,10,10) | 80% |
| (13,10,10) | 40% |
| ... | ... |

77

| POSITION COORDINATES | ADOPTION OR REJECTION OF LABEL |
|---|---|
| ... | ... |
| (10,10,10) | ADOPTED |
| (11,10,10) | ADOPTED |
| (12,10,10) | NOT ADOPTED |
| (13,10,10) | NOT ADOPTED |
| ... | ... |

MORE THAN OR EQUAL TO 20 YEARS OF SERVICE → +0.5
LESS THAN 5 YEARS OF SERVICE → −0.5
QUALIFIED PERSON → +0.5

| ANNOTATOR ID | ATTRIBUTE | | COUNT NUMBER |
| --- | --- | --- | --- |
| | YEARS OF SERVICE | QUALIFICATION | |
| AN0001 | 22 | RADIOLOGY TRAINING INSTRUCTOR | 2 |
| AN0002 | 18 | RADIOLOGICAL DIAGNOSIS SPECIALIST | 1.5 |
| ⋯ | | | |
| AN0100 | 14 | − | 1 |
| AN0101 | 3 | − | 0.5 |
| ⋯ | | | |

130

131

131A

131B

RELIABILITY DISPLAY
VALUE OF LABEL: 0.8

RELIABILITY DISPLAY
VALUE OF LABEL: 1.0

IN CASE WHERE CLASS IS
BLOOD VESSEL, ASSIGN LABEL
TO EXPANSION REGION LARGER
THAN REGION SATISFYING
CONFIRMATION CONDITION

135

135

136

INFORMATION
TRANSMISSION UNIT    140

ANNOTATION INFORMATION    21

CONFIRMED ANNOTATION INFORMATION    42

ANNOTATOR
TERMINAL    11

1

MACHINE LEARNING MODEL CREATION SUPPORT APPARATUS, METHOD OF OPERATING MACHINE LEARNING MODEL CREATION SUPPORT APPARATUS, AND PROGRAM FOR OPERATING MACHINE LEARNING MODEL CREATION SUPPORT APPARATUS

CROSS-REFERENCE TO RELATED APPLICATIONS

This application is a continuation application of International Application No. PCT/JP2022/008070 filed on Feb. 25, 2022, the disclosure of which is incorporated herein by reference in its entirety. Further, this application claims priority from Japanese Patent Application No. 2021-057322 filed on Mar. 30, 2021, the disclosure of which is incorporated herein by reference in its entirety.

BACKGROUND

1. Technical Field

The technique of the present disclosure relates to a machine learning model creation support apparatus, a method of operating a machine learning model creation support apparatus, and a program for operating a machine learning model creation support apparatus.

2. Description of the Related Art

For example, a machine learning model has been developed for recognizing an object appearing in a medical image, such as recognizing a tumor in an abdominal tomographic image captured by a computed tomography (CT) apparatus in units of pixels. In such a machine learning model, annotation information as correct answer data is required in a learning phase or an accuracy evaluation phase. The annotation information is information generated by assigning a label according to a class that is an object to be recognized to an original image paired in the correct answer data. In the example of the abdominal tomographic image, the annotation information is information generated by assigning a label "tumor" to a pixel of the tumor in the abdominal tomographic image which is the original image. WO 2019/003485 A discloses that generation of annotation information is shared by a plurality of annotators. Specifically, the same original image is transmitted to respective annotator terminals of the plurality of annotators, and a plurality of pieces of annotation information generated by the plurality of annotators assigning labels to the original image are received from the plurality of annotator terminals.

SUMMARY

An embodiment according to the technique of the present disclosure provides a machine learning model creation support apparatus, a method of operating a machine learning model creation support apparatus, and a program for operating a machine learning model creation support apparatus capable of easily obtaining appropriate annotation information used as correct answer data of a machine learning model.

A machine learning model creation support apparatus according to the present disclosure including a processor, in which the processor acquires a plurality of pieces of annotation information generated by a plurality of annotators assigning a plurality of labels according to a plurality of classes to a region of the same medical image, derives, for each of the classes, commonality data indicating commonality in how the labels are assigned by the plurality of annotators for the plurality of pieces of annotation information, and generates confirmed annotation information used as correct answer data of a machine learning model based on the commonality data and a preset confirmation condition.

A method of operating a machine learning model creation support apparatus according to the present disclosure, the method including: acquiring a plurality of pieces of annotation information generated by a plurality of annotators assigning a plurality of labels according to a plurality of classes to a region of the same medical image; deriving, for each of the classes, commonality data indicating commonality in how the labels are assigned by the plurality of annotators for the plurality of pieces of annotation information; and generating confirmed annotation information used as correct answer data of a machine learning model based on the commonality data and a preset confirmation condition.

A program for operating a machine learning model creation support apparatus according to the present disclosure, the program causing a computer to execute processing of: acquiring a plurality of pieces of annotation information generated by a plurality of annotators assigning a plurality of labels according to a plurality of classes to a region of the same medical image; deriving, for each of the classes, commonality data indicating commonality in how the labels are assigned by the plurality of annotators for the plurality of pieces of annotation information; and generating confirmed annotation information used as correct answer data of a machine learning model based on the commonality data and a preset confirmation condition.

BRIEF DESCRIPTION OF THE DRAWINGS

Exemplary embodiments according to the technique of the present disclosure will be described in detail based on the following figures, wherein:

FIG. 5 is a block diagram illustrating a processing unit of a processor of the machine learning model creation support server;

FIG. 8 is a diagram illustrating annotation information in which labels of different classes are assigned to the same region;

FIG. 9 is a diagram illustrating another example of a confirmation condition and processing of a derivation unit and a generation unit;

FIG. 16 is a diagram illustrating annotator information;

DETAILED DESCRIPTION

First Embodiment

Figure 1:
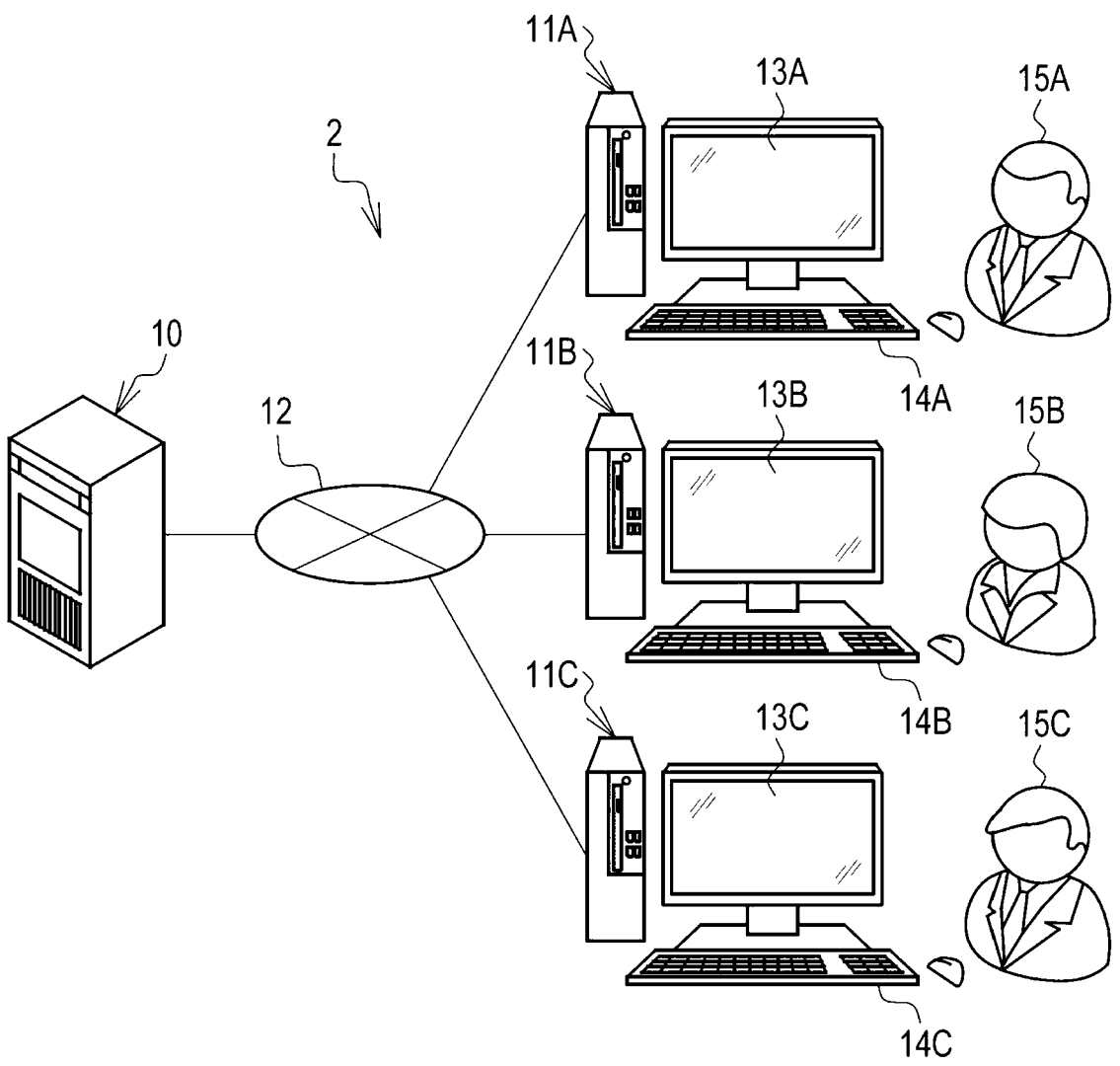
FIG. 1 is a diagram illustrating a machine learning model creation support system.

As an example, as illustrated in FIG. 1, a machine learning model creation support system 2 includes a machine learning model creation support server (hereinafter, abbreviated as a support server) 10 and annotator terminals 11A, 11B, and 11C. The support server 10 and the annotator terminals 11A to 11C are communicably connected to each other via a network 12. The network 12 is, for example, the Internet or a wide area network (WAN).

The support server 10 is, for example, a server computer, a workstation, or the like, and is an example of a "machine learning model creation support apparatus" according to the technique of the present disclosure. The annotator terminal 11A includes a display 13A and an input device 14A, the annotator terminal 11B includes a display 13B and an input device 14B, and the annotator terminal 11C includes a displays 13C and an input device 14C. The annotator terminal 11A is operated by an annotator 15A, the annotator terminal 11B is operated by an annotator 15B, and the annotator terminal 11C is operated by an annotator 15C. The annotator terminals 11A to 11C are, for example, personal computers, tablet terminals, or the like. The annotators 15A to 15C are, for example, doctors, and are requested by the support server 10 to generate the annotation information 21 (see FIG. 2). Note that, in a case where it is not particularly necessary to distinguish them, the annotator terminals 11A to 11C are collectively referred to as the annotator terminals 11. Similarly, the displays 13A to 13C, the input devices 14A to 14C, and the annotators 15A to 15C may be collectively referred to as the displays 13, the input devices 14, and the annotators 15. Note that the input device 14 is, for example, at least one of a keyboard, a mouse, a touch panel, a microphone, a gesture recognition device, or the like.

Figure 2:
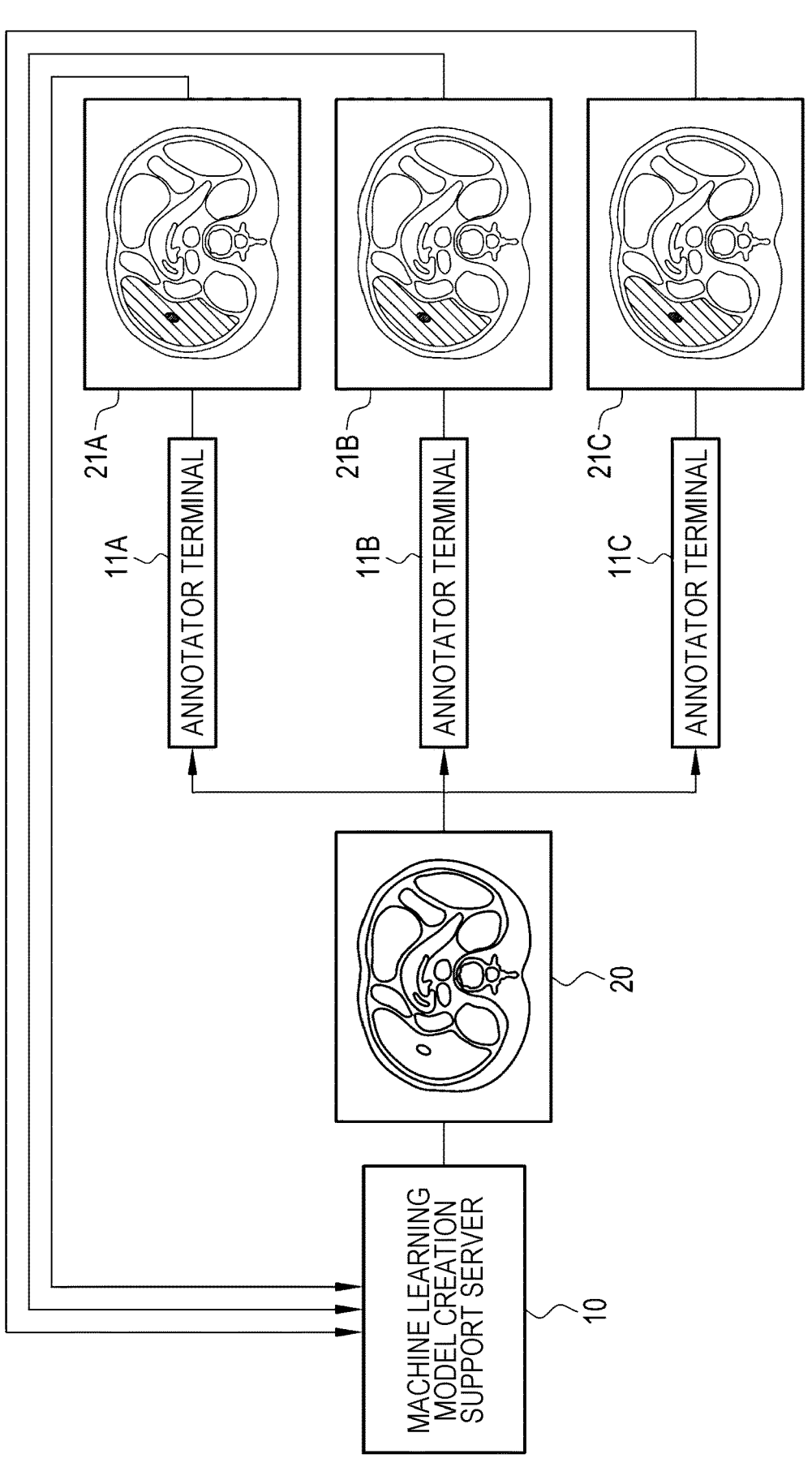
FIG. 2 is a diagram illustrating a medical image and annotation information transmitted and received between a machine learning model creation support server and an annotator terminal.

As an example, as illustrated in FIG. 2, the support server 10 transmits the same medical image 20 to the annotator terminals 11A to 11C. Here, an abdominal tomographic image of an axial cross section captured by a CT apparatus is exemplified as the medical image 20. The medical image 20 is an original image for assigning a label according to a class that is an object to be recognized based on a task set in advance. Note that the same medical image 20 refers to a medical image 20 in which a medical image capturing apparatus (also referred to as a modality) such as a CT apparatus, a patient, and an imaging date and time are the same.

Each of the annotator terminal 11 displays the medical image 20 on each of the displays 13. The annotator terminal 11 receives an input of the assignment of the label in units of pixels of the medical image 20 from the annotator 15 through the input device 14. In this way, annotation information 21A is generated by the annotator 15A in the annotator terminal 11A, annotation information 21B is generated by the annotator 15B in the annotator terminal 11B, and annotation information 21C is generated by the annotator 15C in the annotator terminal 11C. Note that similarly to the annotator terminals 11A to 11C, the annotation information 21A to 21C may be collectively referred to as the annotation information 21.

Since the medical image 20 in this example is an abdominal tomographic image, the annotation information 21 is generated for each tomographic plane of the abdominal tomographic image. Note that in FIG. 2, for ease of understanding, the human body structure is depicted in the annotation information 21, but the actual annotation information 21 does not include data of the human body structure, but only includes data of the assigned label (The same applies to FIG. 3 and the like). More specifically, the annotation information 21 is information in which a set of a type of the label and position coordinates of the pixel of the medical image 20 to which the label is assigned is registered.

The annotator terminal 11 transmits the annotation information 21 to the support server 10. The support server 10 receives the annotation information 21 from the annotator terminal 11.

Figure 3:
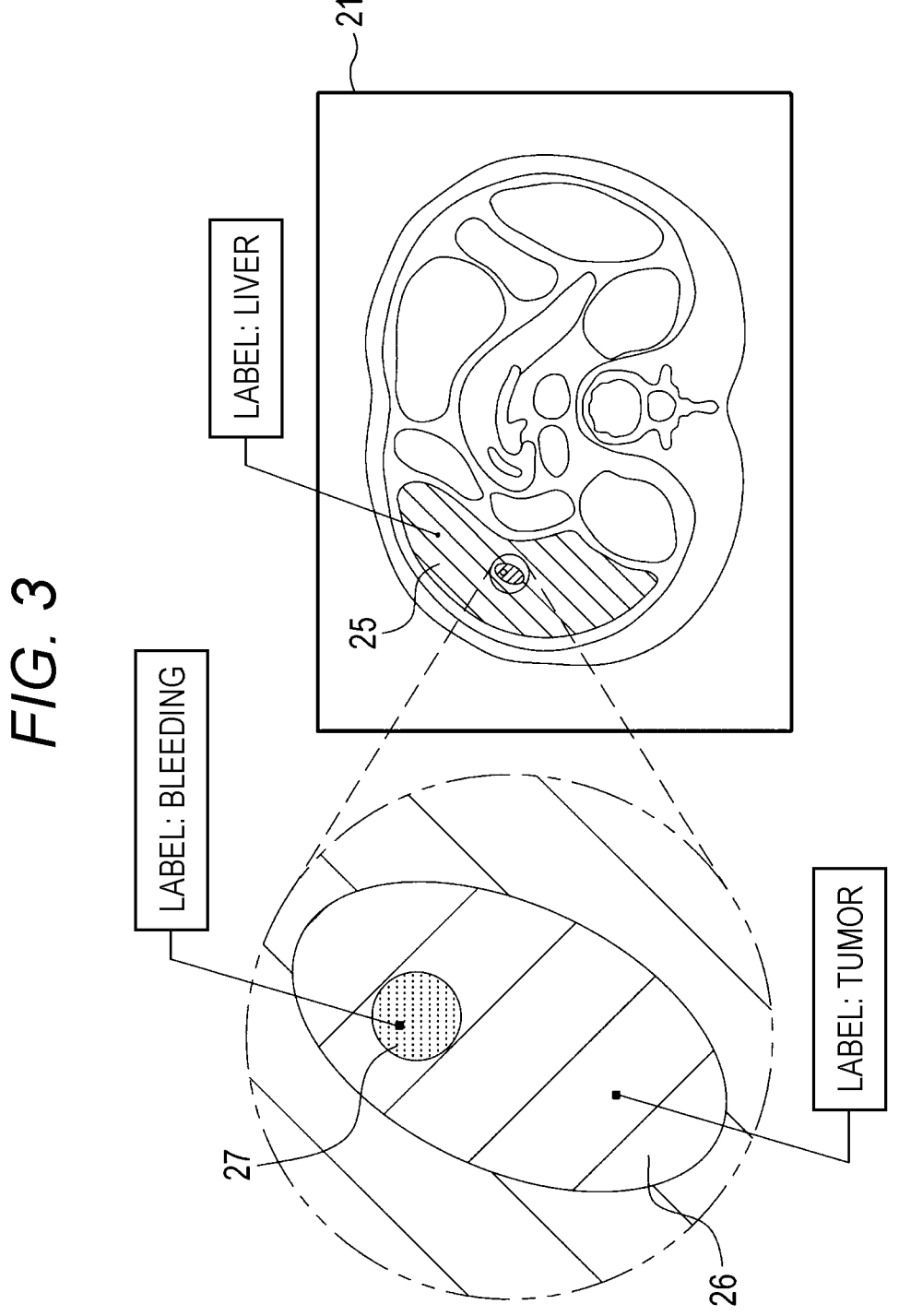
FIG. 3 is a diagram illustrating annotation information.

The three classes set in the task of this example are a liver, a tumor in the liver, and a bleeding site in the tumor. Therefore, as an example, as illustrated in FIG. 3, the annotation information 21 includes a first region 25 to which a label of a liver is assigned, a second region 26 to which a label of a tumor is assigned, and a third region 27 to which a label of bleeding is assigned. Note that the second region 26 is naturally not designated in a case where the annotator 15 determines that there is no tumor. Similarly, the third region 27 is not designated in a case where the annotator 15 determines that the bleeding site does not exist.

Figure 4:
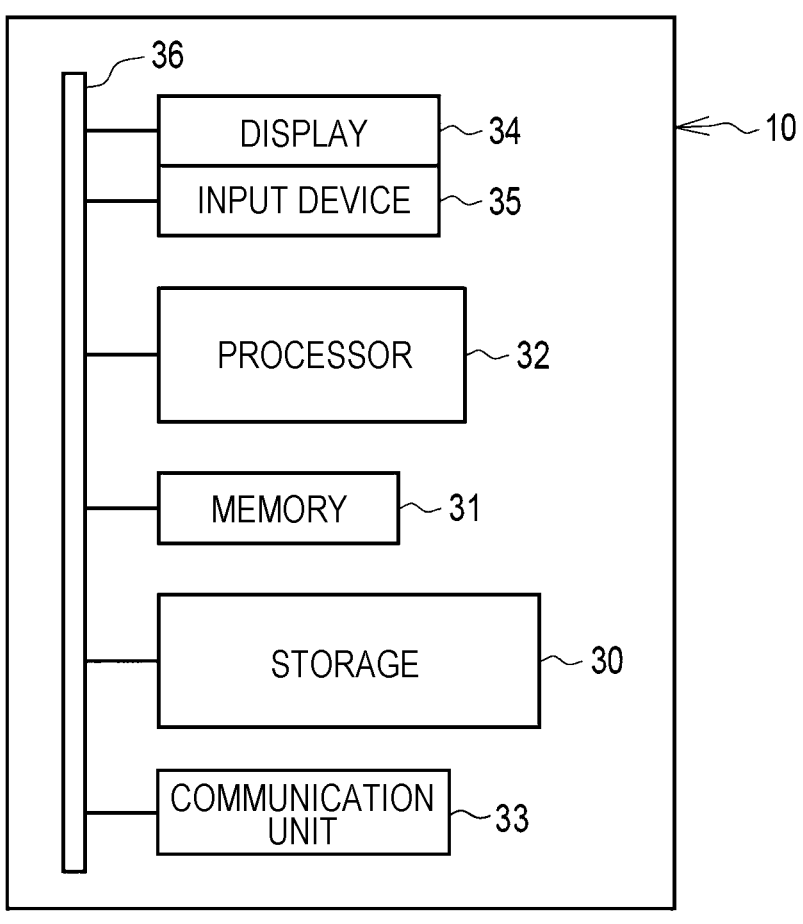
FIG. 4 is a block diagram illustrating a computer constituting the machine learning model creation support server.

As an example, as illustrated in FIG. 4, a computer constituting the support server 10 includes a storage 30, a memory 31, a processor 32, a communication unit 33, a display 34, and an input device 35. These units are connected to each other through a bus line 36.

The storage 30 is a hard-disk drive that is incorporated in the computer constituting the support server 10 or is connected to the computer through a cable or a network. Alternatively, the storage 30 is a disk array in which a plurality of hard-disk drives are continuously connected. The storage 30 stores a control program such as an operating system, various application programs (hereinafter, abbreviated as an application program (AP)), various data associated with these programs, and the like. Note that a solid-state drive may be used instead of the hard-disk drive.

The memory 31 is a working memory for the processor 32 to execute processing. The memory 31 is, for example, a random-access memory (RAM) such as a dynamic random-access memory (DRAM) or a static random-access memory (SRAM). The processor 32 loads the program stored in the storage 30 to the memory 31 and executes processing according to the program. Thus, the processor 32 integrally controls each unit of the computer. The processor 32 is, for example, a central processing unit (CPU). Furthermore, the memory 31 is an example of a "memory" according to the technique of the present disclosure. Note that the storage 30 or both the storage 30 and the memory 31 may be defined as an example of a "memory" according to the technique of the present disclosure.

The communication unit 33 is a network interface that controls transmission of various kinds of information through the network 12 or the like. The display 34 displays various screens. The various screens are provided with an operation function by a graphical user interface (GUI). The computer constituting the support server 10 receives an input of an operation instruction from the input device 35 through various screens. The input device 35 is at least one of a keyboard, a mouse, a touch panel, a microphone, a gesture recognition device, or the like.

Figure 5:
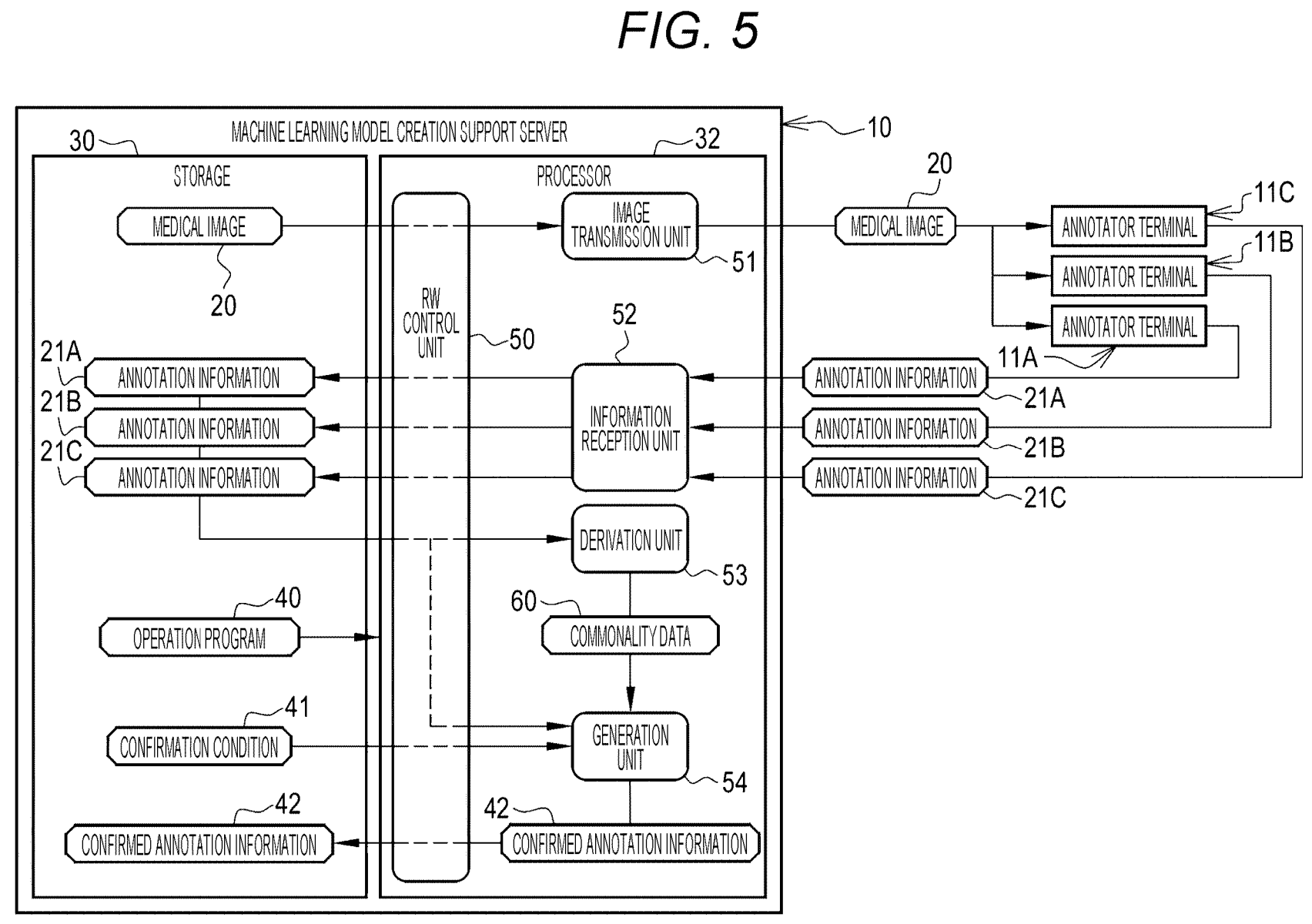

For example, as illustrated in FIG. 5, an operation program 40 is stored in the storage 30. The operation program 40 is an AP for causing the computer constituting the support server 10 to function as a "machine learning model creation support apparatus" according to the technique of the present disclosure. That is, the operation program 40 is an example of a "program for operating a machine learning model creation support apparatus" according to the technique of the present disclosure. In addition to the operation program 40, the medical image 20, the annotation information 21, a confirmation condition 41, and confirmed annotation information 42 are also stored in the storage 30. Note that, although only one medical image 20 is depicted, a plurality of the medical images 20 are actually stored in the storage 30. The same applies to the annotation information 21 and the confirmed annotation information 42.

In a case where the operation program 40 is activated, the processor 32 cooperates with the memory 31 and the like to function as a read and write (hereinafter abbreviated as RW) control unit 50, an image transmission unit 51, an information reception unit 52, a derivation unit 53, and a generation unit 54.

The RW control unit 50 controls storage of various kinds of information in the storage 30 and reading of various kinds of information in the storage 30. For example, the RW control unit 50 reads out the medical image 20 from the storage 30 and outputs the read medical image to the image transmission unit 51. Furthermore, the RW control unit 50 reads out the confirmation condition 41 from the storage 30 and outputs the read confirmation condition 41 to the generation unit 54.

Information of the annotator terminal 11 that transmits the medical image 20 is registered in the storage 30 in advance. The image transmission unit 51 transmits the medical image 20 from the RW control unit 50 to the annotator terminal 11 registered in advance.

The information reception unit 52 receives the annotation information 21 from the annotator terminal 11. Accordingly, the support server 10 acquires the annotation information 21. The information reception unit 52 outputs the received annotation information 21 to the RW control unit 50. The RW control unit 50 stores the annotation information 21 in the storage Note that, in FIG. 5, although it is depicted that the information reception unit 52 receives the annotation information 21A to 21C at the same time, in reality, the reception timings of the annotation information 21A to 21C are different. The information reception unit 52 outputs the annotation information 21 to the RW control unit 50 every time the annotation information 21 is received, and the RW control unit 50 stores the annotation information 21 in the storage 30 every time the annotation information 21 is input from the information reception unit 52.

In a case where the annotation information 21A to 21C is stored in the storage 30, the RW control unit 50 reads the annotation information 21A to 21C from the storage 30 and outputs the read annotation information 21A to 21C to the derivation unit 53 and the generation unit 54.

The derivation unit 53 derives commonality data 60. The commonality data 60 is a data for indicating commonality of the ways of assigning labels by the three annotators 15A to 15C for the three pieces of annotation information 21A to 21C. The derivation unit 53 outputs the derived commonality data 60 to the generation unit 54.

The generation unit 54 generates the confirmed annotation information 42 based on the commonality data 60 from the derivation unit 53, the annotation information 21A to 21C from the RW control unit 50, and the confirmation condition 41. The confirmed annotation information 42 is annotation information that is ultimately used as correct answer data of a machine learning model. The generation unit 54 outputs the confirmed annotation information 42 to the RW control unit 50. The RW control unit 50 stores the confirmed annotation information 42 from the generation unit 54 in the storage 30.

The confirmed annotation information 42 is used as correct answer data together with the medical image 20, which is an original image, in a learning phase or an accuracy evaluation phase of the machine learning model. In the learning phase, the medical image 20 is input to the machine learning model. Next, the output annotation information output from the machine learning model is compared with the confirmed annotation information 42, and the loss of the machine learning model is calculated. The machine learning model is updated according to the loss. The loss decreases as a difference between the output annotation information and the confirmed annotation information 42 decreases. Therefore, the degree of update also decreases as the difference between the output annotation information and the confirmed annotation information 42 decreases. The input of the medical image 20, the output of the output annotation information, the calculation of the loss, and the update are repeated while a set of the medical image 20 and the confirmed annotation information 42, that is, correct answer data, is exchanged. Accordingly, the machine learning model is trained.

In the accuracy evaluation phase, the medical image 20 is input to the machine learning model that has undergone a certain degree of training. Then, the output annotation information output from the machine learning model is compared with the confirmed annotation information 42 to calculate the loss, and the accuracy of the machine learning model is evaluated based on the loss. In the accuracy evaluation phase, only the accuracy is evaluated, and the update is not performed. The machine learning model determined to have an accuracy equal to or higher than a preset accuracy in the accuracy evaluation phase is used in a practical phase. Note that the correct answer data used in the learning phase is also referred to as training data, and the correct answer data used in the accuracy evaluation phase is also referred to as evaluation data.

Figure 6:
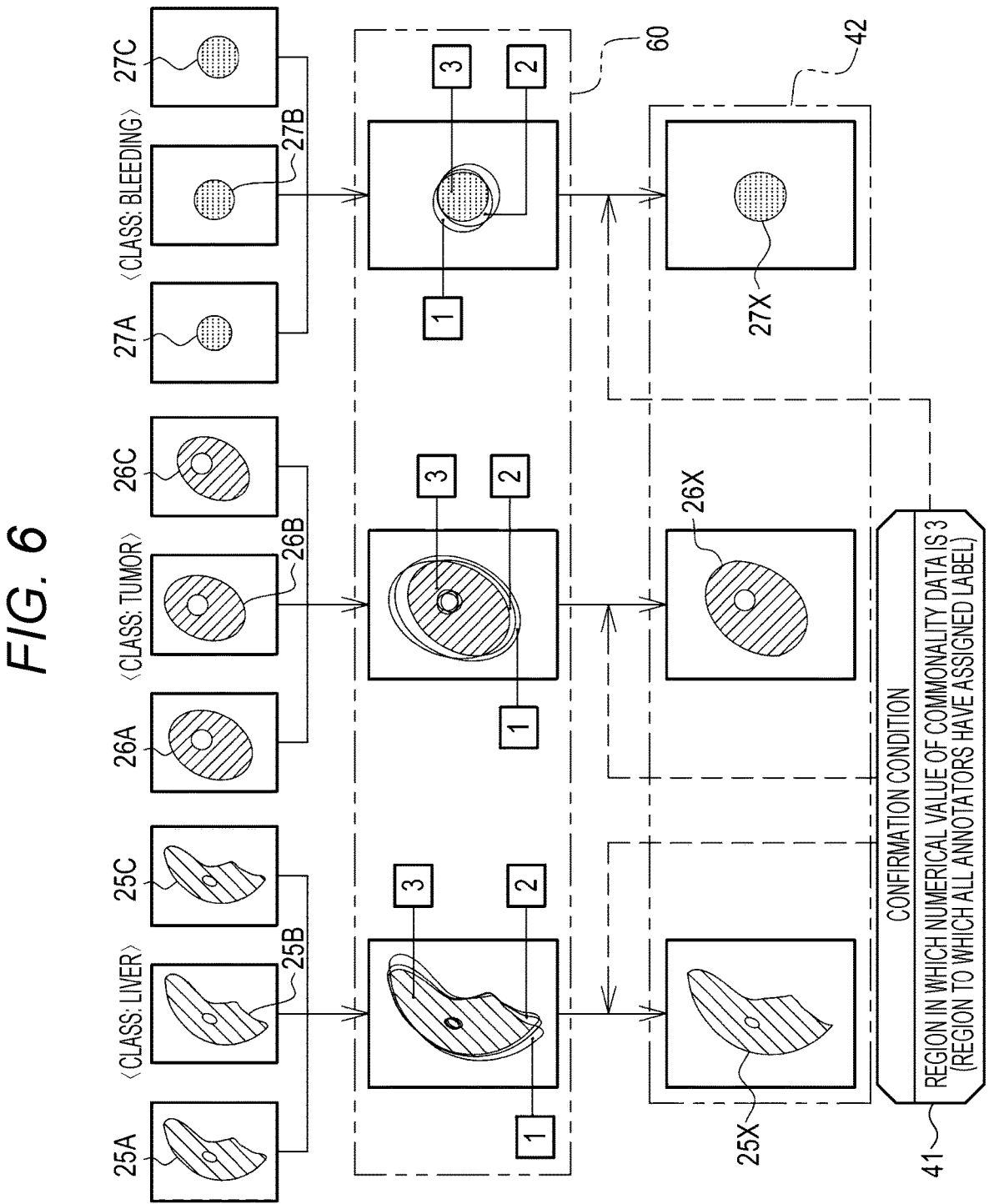
FIG. 6 is a diagram illustrating a confirmation condition and processing of a derivation unit and a generation unit.

As an example, as illustrated in FIG. 6, a first region 25A is a region to which a label of a liver is assigned in the annotation information 21A, a first region 25B is a region to which the label of the liver is assigned in the annotation information 21B, and a first region 25C is a region to which the label of the liver is assigned in the annotation information 21C. Furthermore, a second region 26A is a region to which a label of a tumor is assigned in the annotation information 21A, a second region 26B is a region to which the label of the tumor is assigned in the annotation information 21B, and a second region 26C is a region to which the label of the tumor is assigned in the annotation information 21C. Moreover, a third region 27A is a region to which a label of bleeding is assigned in the annotation information 21A, a third region 27B is a region to which the label of bleeding is assigned in the annotation information 21B, and a third region 27C is a region to which the label of bleeding is assigned in the annotation information 21C.

The derivation unit 53 counts the number of persons of the annotators 15 who have assigned each of the labels of the liver, the tumor, and the bleeding, and sets the counted number of persons as the numerical value of the commonality data 60. The numerical value of the commonality data 60 of a pixel to which the label has been assigned by one annotator 15 is 1, and the numerical value of the commonality data 60 of a pixel to which the labels have been assigned by the two annotators 15 is 2. Furthermore, the numerical value of the commonality data 60 of a pixel to which the labels have been assigned by the three annotators 15 is 3. The derivation unit 53 derives the commonality data 60 for each class of the liver, the tumor, and the bleeding. Note that the number of persons of the annotators 15 who have assigned the labels is an example of a "numerical value related to the number of persons of the annotators who have assigned the labels" according to the technique of the present disclosure.

The confirmation condition 41 according to the present embodiment is that a label of a region in which the numerical value of the commonality data 60 is 3, that is, a label of a region to which all the annotators 15 have assigned labels, is adopted. Therefore, the generation unit 54 generates the confirmed annotation information 42 including a first region 25X to which the three annotators 15 have assigned the labels of the liver, a second region 26X to which the three annotators 15 have assigned the labels of the tumor, and a third region 27X to which the three annotators 15 have assigned the labels of the bleeding.

Figure 7:
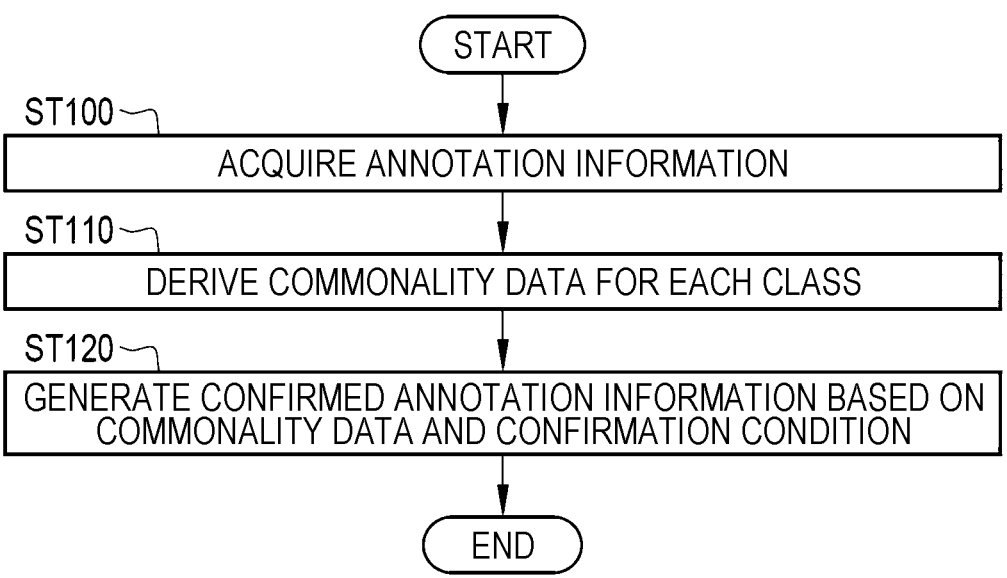
FIG. 7 is a flowchart illustrating a processing procedure of the machine learning model creation support server.

Next, an action of the above-described configuration will be described referring to a flowchart of FIG. 7. In a case where the operation program 40 is activated, the processor 32 of the support server 10 functions as the RW control unit 50, the image transmission unit 51, the information reception unit 52, the derivation unit 53, and the generation unit 54 as illustrated in FIG. 5.

First, the RW control unit 50 reads out the medical image 20 from the storage 30. The read medical image 20 is output from the RW control unit 50 to the image transmission unit 51. The medical image 20 is transmitted to the annotator terminal 11 by the image transmission unit 51.

In the annotator terminal 11, the annotation information 21 is generated on the basis of the medical image 20 by the annotator 15. As illustrated in FIG. 3, the annotation information 21 is generated by assigning three labels corresponding to three classes of a liver, a tumor, and bleeding to the regions of the same medical image 20. The annotation information 21 is transmitted from the annotator terminal 11 to the support server 10.

In the support server 10, the information reception unit 52 receives the annotation information 21 from the annotator terminal 11. Accordingly, the annotation information 21 is acquired (step ST100). The annotation information 21 is output from the information reception unit 52 to the RW control unit 50, and is stored in the storage 30 by the RW control unit 50. The RW control unit 50 reads the annotation information 21 from the storage 30. The read annotation information 21 is output from the RW control unit 50 to the derivation unit 53 and the generation unit 54.

As illustrated in FIG. 6, the derivation unit 53 derives, for each of the classes, the commonality data 60 indicating commonality in how labels are assigned by the plurality of annotators 15A to 15C for the plurality of pieces of annotation information 21A to 21C (step ST110). The commonality data 60 is a count value of the number of persons of the annotators 15 who have assigned the respective labels of the liver, the tumor, and the bleeding. The commonality data 60 is output from the derivation unit 53 to the generation unit 54.

As illustrated in FIG. 6, the generation unit 54 generates the confirmed annotation information 42 on the basis of the commonality data 60 and the confirmation condition 41 (step ST120). In this example, the confirmed annotation information 42 including the first region 25X, the second region 26X, and the third region 27X to which the labels of the liver, the tumor, and the bleeding have been assigned by the three annotators 15 is generated. The confirmed annotation information 42 is output from the generation unit 54 to the RW control unit 50, and is stored in the storage 30 by the RW control unit 50.

As described above, the processor 32 of the support server 10 includes the information reception unit 52, the derivation unit 53, and the generation unit 54. The information reception unit 52 acquires the annotation information by receiving the annotation information 21A to 21C from the annotator terminals 11A to 11C. The annotation information 21A to 21C is generated by the annotators 15A to 15C assigning the three labels corresponding to the three classes to the regions of the same medical image 20. The derivation unit 53 derives, for each of the classes, the commonality data 60 indicating the commonality in how labels are assigned by the annotators 15A to 15C for the annotation information 21A to 21C. The generation unit 54 generates the confirmed annotation information 42 to be used as correct answer data of the machine learning model based on the commonality data 60 and the confirmation condition 41 set in advance.

In a case where the generation of the annotation information 21 for the same medical image 20 is shared by the plurality of annotators 15, a difference occurs between the plurality of pieces of annotation information 21 because the way of assigning the label differs depending on the annotators 15. In the technique of the present disclosure, since the annotation information 21 is generated by assigning the plurality of labels corresponding to the plurality of classes, the difference between the plurality of pieces of annotation information 21 becomes larger as the number of labels to be assigned increases.

Therefore, in the technique of the present disclosure, the commonality data 60 is derived for each class, and the confirmed annotation information 42 is generated based on the derived commonality data 60. Therefore, it is possible to easily obtain appropriate confirmed annotation information 42 used as correct answer data of the machine learning model.

Second Embodiment

Figure 8:
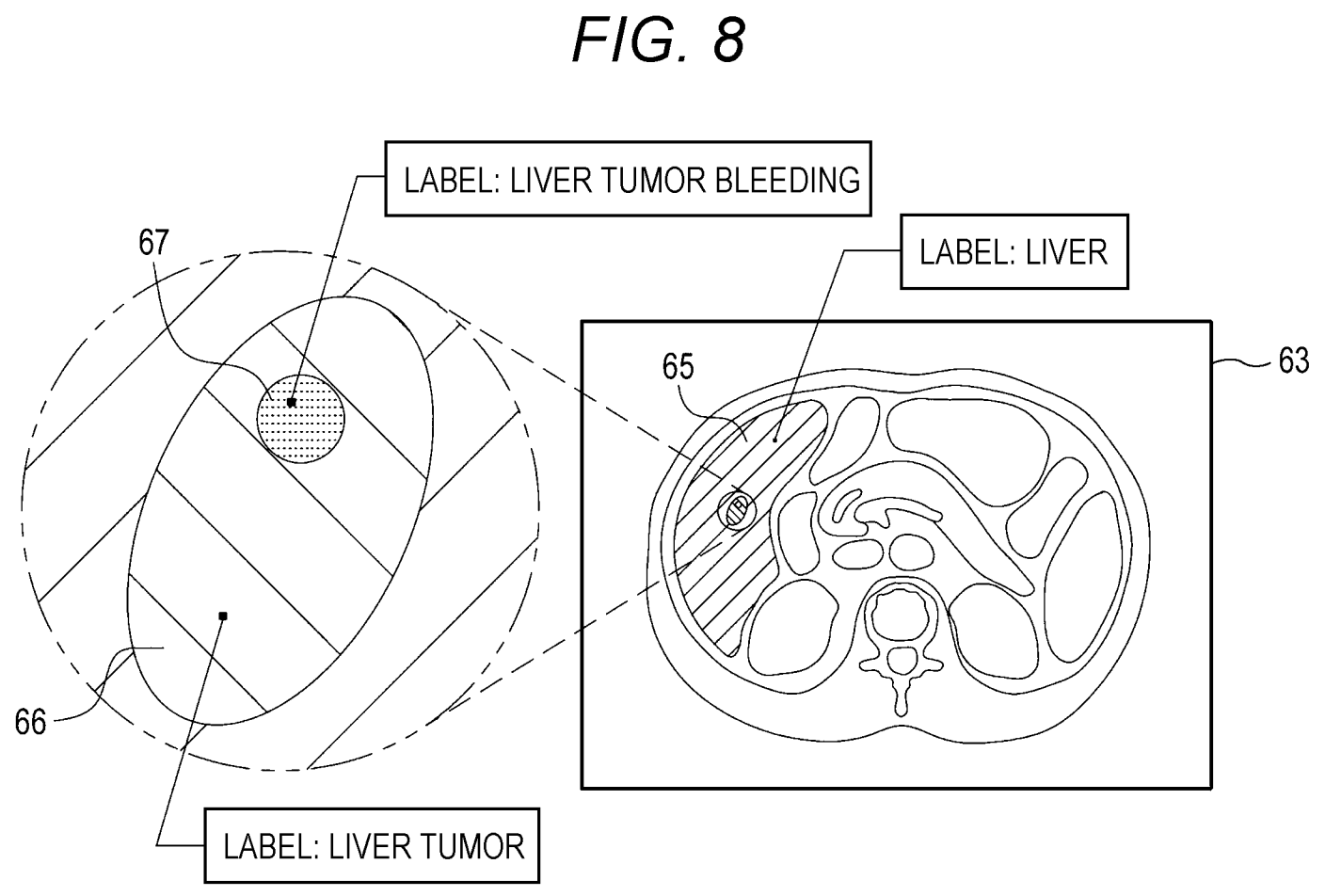

As an example, as illustrated in FIG. 8, annotation information 63 of the present embodiment includes a first region 65 to which a label of a liver is assigned, a second region 66 to which labels of the liver and a tumor are assigned, and a third region 67 to which labels of the liver, the tumor, and bleeding are assigned. The second region 66 and the third region 67 are regions to which the labels of different classes are assigned.

As described above, in the second embodiment, the annotation information 63 is information in which the labels of different classes are assigned to the same region. Therefore, as the number of types of labels assigned to the same region increases, the difference between the plurality of pieces of annotation information 21 becomes larger than that in the first embodiment. Therefore, it is possible to further exhibit an effect of easily obtaining appropriate confirmed annotation information 42 used as correct answer data of the machine learning model.

Third_1 Embodiment

As an example, as illustrated in FIG. 9, the contents of a confirmation condition 70 of the present embodiment is that a label of a region in which the numerical value of the commonality data 60 is greater than or equal to 2, that is, a label of a region to which the number of persons of the annotators who have assigned a label is greater than or equal to 2, is adopted. Therefore, the generation unit 54 generates the confirmed annotation information 42 including the first region 25Y to which the labels of the liver have been assigned by two or more annotators 15, the second region (not illustrated) to which the labels of the tumor have been assigned by two or more annotators 15, and the third region (not illustrated) to which the labels of the bleeding have been assigned by two or more annotators 15. Note that "2" or "two persons" in the confirmation condition 70 is an example of a "threshold value" according to the technique of the present disclosure.

Third_2 Embodiment

Figure 10:
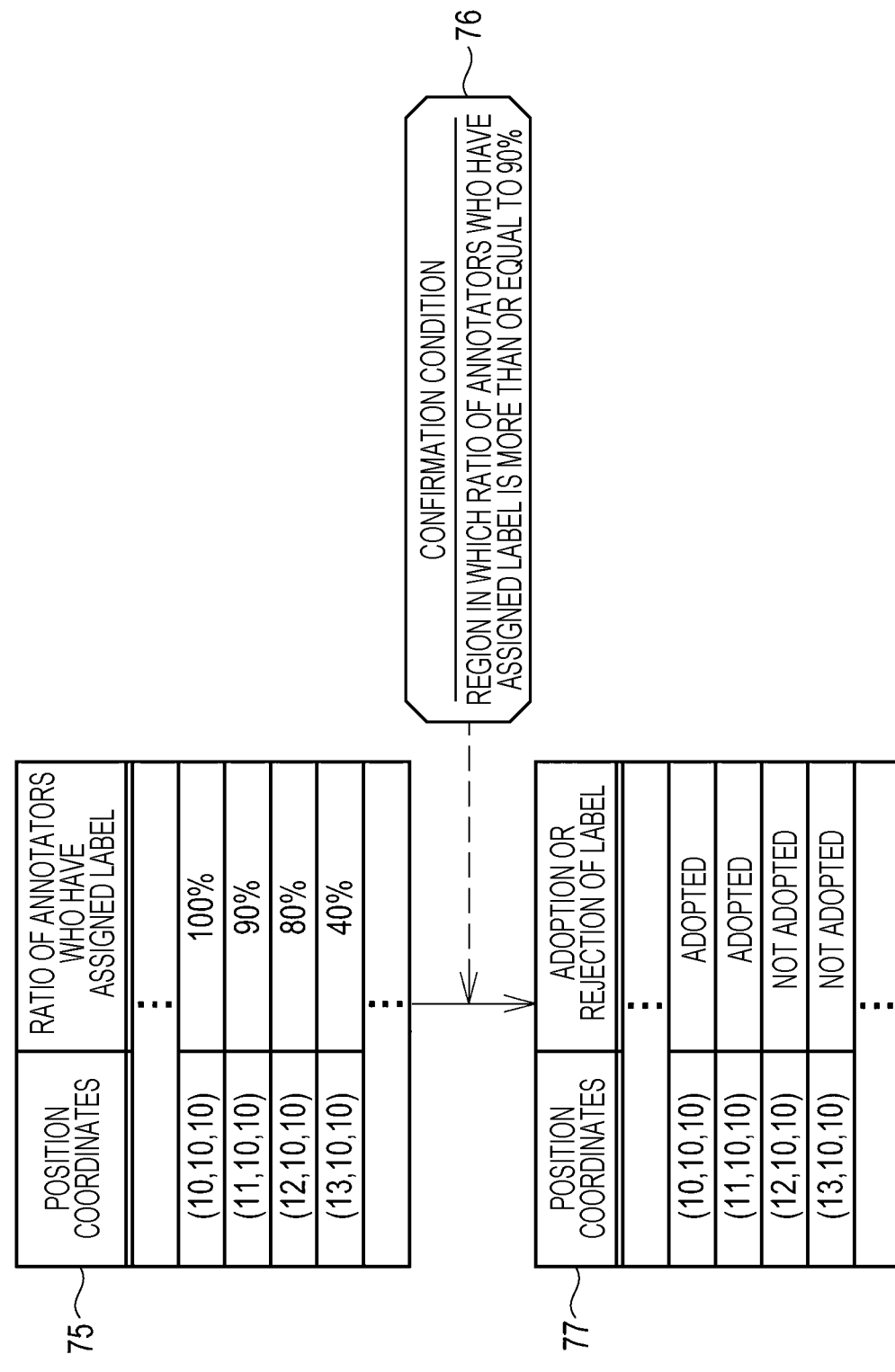
FIG. 10 is a diagram illustrating another example of commonality data, a confirmation condition, and processing of a derivation unit and a generation unit.

For example, as illustrated in FIG. 10, the derivation unit 53 (not illustrated) of the present embodiment derives commonality data 75 in which a ratio of the annotators 15 who have assigned the labels is registered for each position coordinate of the pixel to which the labels are assigned. The derivation unit 53 derives the commonality data 75 in which the ratio of the annotators who have assigned the illustrated labels of the liver is registered. Furthermore, the derivation unit 53 also derives the commonality data 75 in which the ratio of the annotators who have assigned the labels of the tumor is registered and the commonality data 75 in which the ratio of the annotators 15 who have assigned the labels of the bleeding is registered (not illustrated). Regarding the ratio of the annotators 15 who have assigned the labels, first, the number of persons of the annotators 15 who have assigned the labels is counted as in the first embodiment. Then, the counted number of persons is divided by the number of persons of all the annotators 15. For example, in a case where the number of persons of the annotators 15 who have assigned the labels is eight and the number of persons of all the annotators is ten, the ratio of the annotators 15 who have assign the labels is ($8/10$)×100=80%. Note that the ratio of the annotators 15 who have assigned the labels is an example of a "numerical value related to the number of persons of the annotators who have assigned the labels" according to the technique of the present disclosure.

The confirmation condition 76 according to the present embodiment is that a label of a region in which a ratio of the annotators 15 who have assigned the labels is more than or equal to 90% is adopted. The generation unit 54 (not illustrated) of the present embodiment determines adoption or rejection of the label for each position coordinate as illustrated in Table 77 based on the commonality data 75 and the confirmation condition 76. Specifically, the generation unit 54 determines to adopt the labels of the position coordinates in which the ratio of the annotators 15 who have assigned the labels of the commonality data 75 is greater than or equal to 90% of the confirmation condition 76. On the other hand, the generation unit 54 determines not to adopt (non-adoption) the labels of the position coordinates in which the ratio of the annotators 15 who have assigned the labels of the commonality data 75 is less than 90% of the confirmation condition 76. The generation unit 54 generates the confirmed annotation information 42 on the basis of the adoption result. Note that "90%" of the confirmation condition 76 is an example of a "threshold value" according to the technique of the present disclosure.

In the case of the first embodiment in which the labels of the region to which all the annotators 15 have assigned the labels are adopted, the confirmed annotation information 42 is inevitably affected by the annotation information 21 in which the region to which the labels have been assigned is relatively small. On the other hand, according to the third_1 embodiment and the third_2 embodiment using the confirmation conditions 70 and 76 indicating that the assigned labels are adopted only in a case where the numerical value of the commonality data 60 or 75 is larger than or equal to the threshold value, it is possible to generate the confirmed annotation information 42 in which the labels have been assigned to a wider region which is not significantly affected by the annotation information 21 in which the region to which the labels have been assigned is relatively small.

Note that, as can be seen from the contents described in the third_2 embodiment, the number of persons of the annotators 15 may be two or more and is not limited to three. Therefore, the number of pieces of annotation information 21 may be two or more, and is not limited to three. Furthermore, a case where the number of persons of the annotators 15 and the confirmation conditions 41, 70, and 76 are fixed has been exemplified, but the present disclosure is not limited thereto. The number of annotators 15 and the confirmation conditions 41, 70, and 76 may be variable. For example, a user who operates the support server 10 may set and change the number of annotators 15 and the confirmation conditions 41, 70, and 76.

Fourth Embodiment

Figure 11:
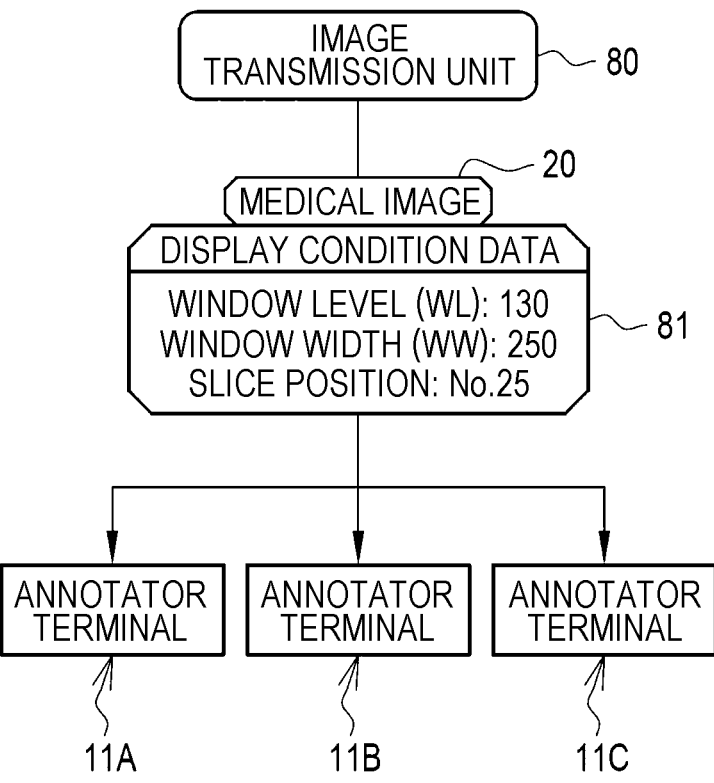
FIG. 11 is a diagram illustrating a fourth embodiment in which display condition data is attached to a medical image.

For example, as illustrated in FIG. 11, an image transmission unit 80 of the present embodiment attaches display condition data 81 to the medical image 20 and transmits the medical image 20 to the annotator terminals 11A to 11C. The display condition data 81 includes a window level (WL), a window width (WW), and a slice position. The window level and the window width are parameters related to the display gradation of the medical image 20. The window level is a central value of a display region of the medical image 20 set with respect to a pixel value of the original image of the medical image 20. The window width is a numerical value indicating a width of the display region of the medical image 20. The slice position indicates a position of a tomographic plane in a case where the medical image 20 is a tomographic image as in the present example.

Figure 12:
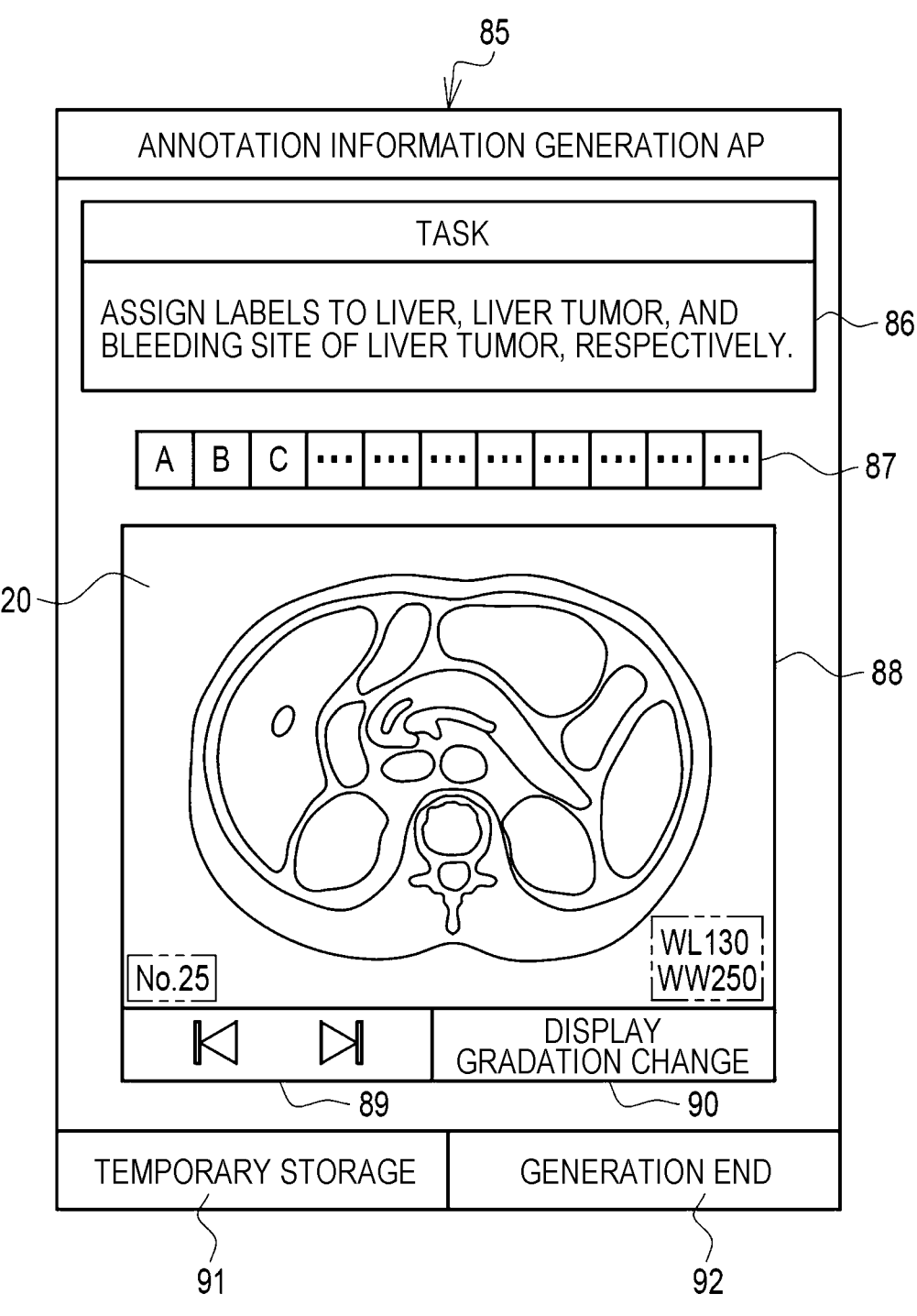
FIG. 12 is a diagram illustrating an annotation information generation screen displayed on a display of the annotator terminal.

As an example, an annotation information generation screen 85 illustrated in FIG. 12 is displayed on the display 13 of the annotator terminal 11. The annotation information generation screen 85 includes a task display region 86, a tool button group 87, and an image display region 88. The contents of the set task are displayed in the task display region 86. The tool button group 87 includes tool buttons of various tools for the annotator 15 to designate a label according to a class designated by a task. The various tools are, for example, a designated class switching tool, a line drawing tool, a region filling tool, and a region erasing tool.

The medical image 20 is displayed in the image display region 88. The annotation information 21 is generated by assigning a label using various tools on the medical image 20 displayed in the image display region 88. As indicated by an enclosure of two dot chain lines, the medical image 20 is initially displayed under the display condition according to the attached display condition data 81. FIG. 12 illustrates an example in which the medical image 20 is displayed under the display conditions according to the display condition data 81 exemplified in FIG. 11.

A feedback button 89 and a display gradation change button 90 are provided in a lower portion of the image display region 88. The slice position can be changed by operating the feedback button 89. Furthermore, the window level and the window width can be changed by operating the display gradation change button 90. In this way, the annotator 15 can freely change the slice position of the medical image 20. Therefore, the annotator 15 can review the medical image 20 at a specific slice position multiple times. Furthermore, the annotator 15 can freely change the display condition of the medical image 20. Note that, although not illustrated, the medical image 20 in the image display region 88 can be translated, and can be enlarged and reduced.

Figure 13:
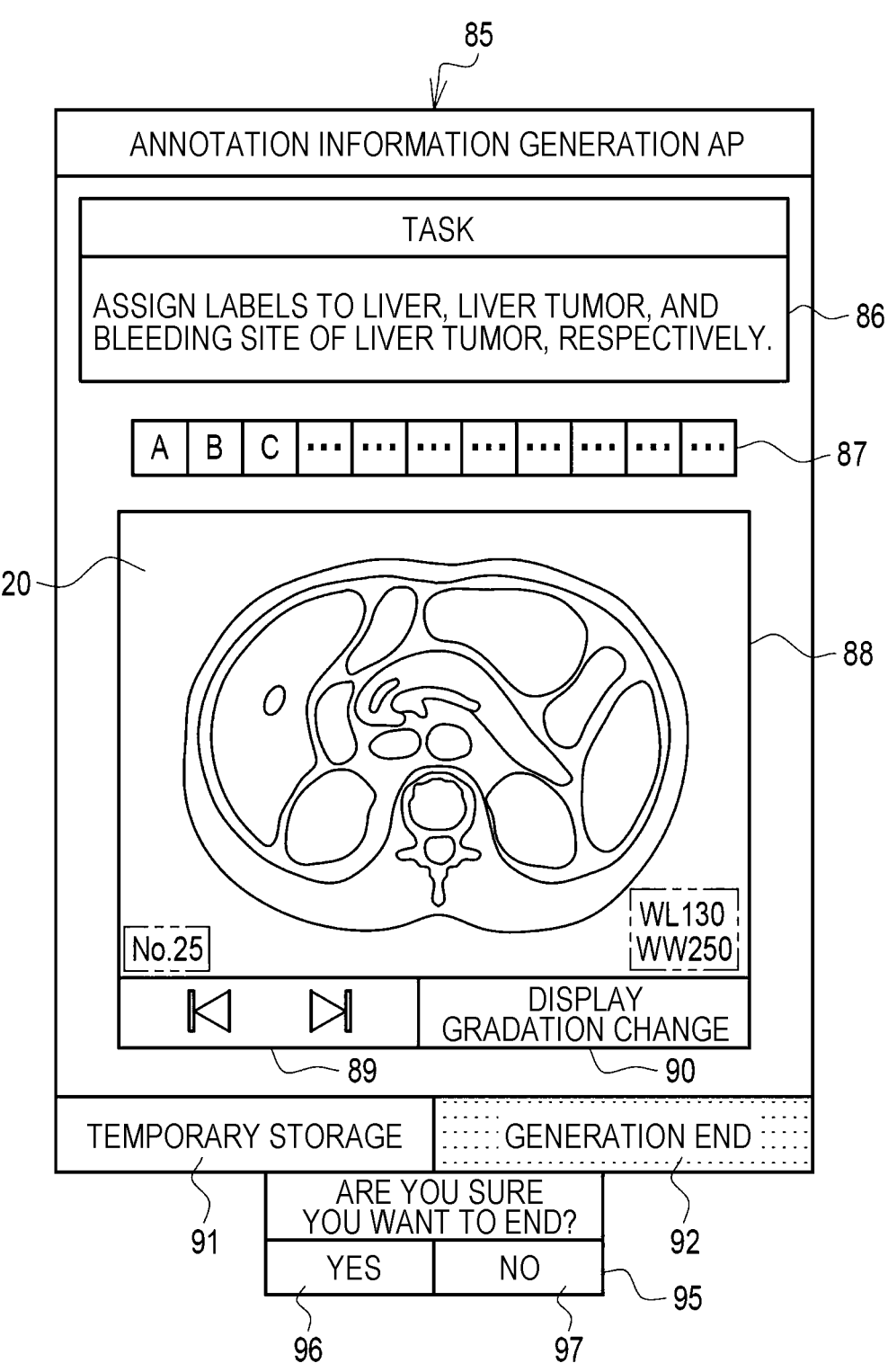
FIG. 13 is a diagram illustrating an annotation information generation screen in a case where a generation end button is operated.

A temporary storage button 91 and a generation end button 92 are further provided in a lower portion of the annotation information generation screen 85. In a case where the temporary storage button 91 is operated, the annotation information 21 generated so far is temporarily stored in a storage of the annotator terminal 11. In a case where the generation end button 92 is operated, for example, as illustrated in FIG. 13, a dialog box 95 is displayed in a pop-up manner. Furthermore, as indicated by an enclosure of two dot chain lines, the display condition of the medical image 20 in the image display region 88 becomes the display condition according to the attached display condition data 81.

The dialog box 95 is a GUI for asking the annotator 15 whether or not to really end the generation of the annotation information 21. The dialog box 95 is provided with a YES button 96 and a NO button 97. In a case where the YES button 96 is operated, the generated annotation information 21 is transmitted to the support server 10. In a case where the NO button 97 is selected, the dialog box 95 is closed, and the state is returned to a state where the annotation information 21 can be generated.

As described above, in the fourth embodiment, the display condition data 81 is attached to the medical image 20. The display condition data 81 is data for displaying the medical image 20 under the same display condition in a case where the plurality of annotators 15 view the medical image 20. Therefore, as illustrated in FIGS. 12 and 13, it is possible to arrange the display conditions to be the same in the plurality of annotator terminals 11. Therefore, it is possible to suppress occurrence of a difference in label assignment by each annotator 15 due to a difference in the display condition.

As illustrated in FIG. 12, by initially displaying the medical image 20 under the display condition according to the display condition data 81, it is possible to suppress the occurrence of a deviation in the recognition of each annotator 15 from the start of the generation of the annotation information 21. Furthermore, as illustrated in FIG. 13, in a case where the generation of the annotation information 21 is ended, the medical image 20 is displayed under the display condition according to the display condition data 81, whereby it is possible to suppress the occurrence of deviation in the recognition of each annotator 15 in the final confirmation of the annotation information 21.

Note that, in the present embodiment, in both a case where the generation of the annotation information 21 is started and a case where the generation of the annotation information 21 is ended, the display condition of the medical image 20 is made the same by displaying the medical image 20 under the display condition according to the display condition data 81, but the present disclosure is not limited thereto. The medical image 20 may be displayed under the display condition according to the display condition data 81 only in any one of a case where the generation of the annotation information 21 is started or a case where the generation of the annotation information 21 is ended.

Fifth Embodiment

Figure 14:
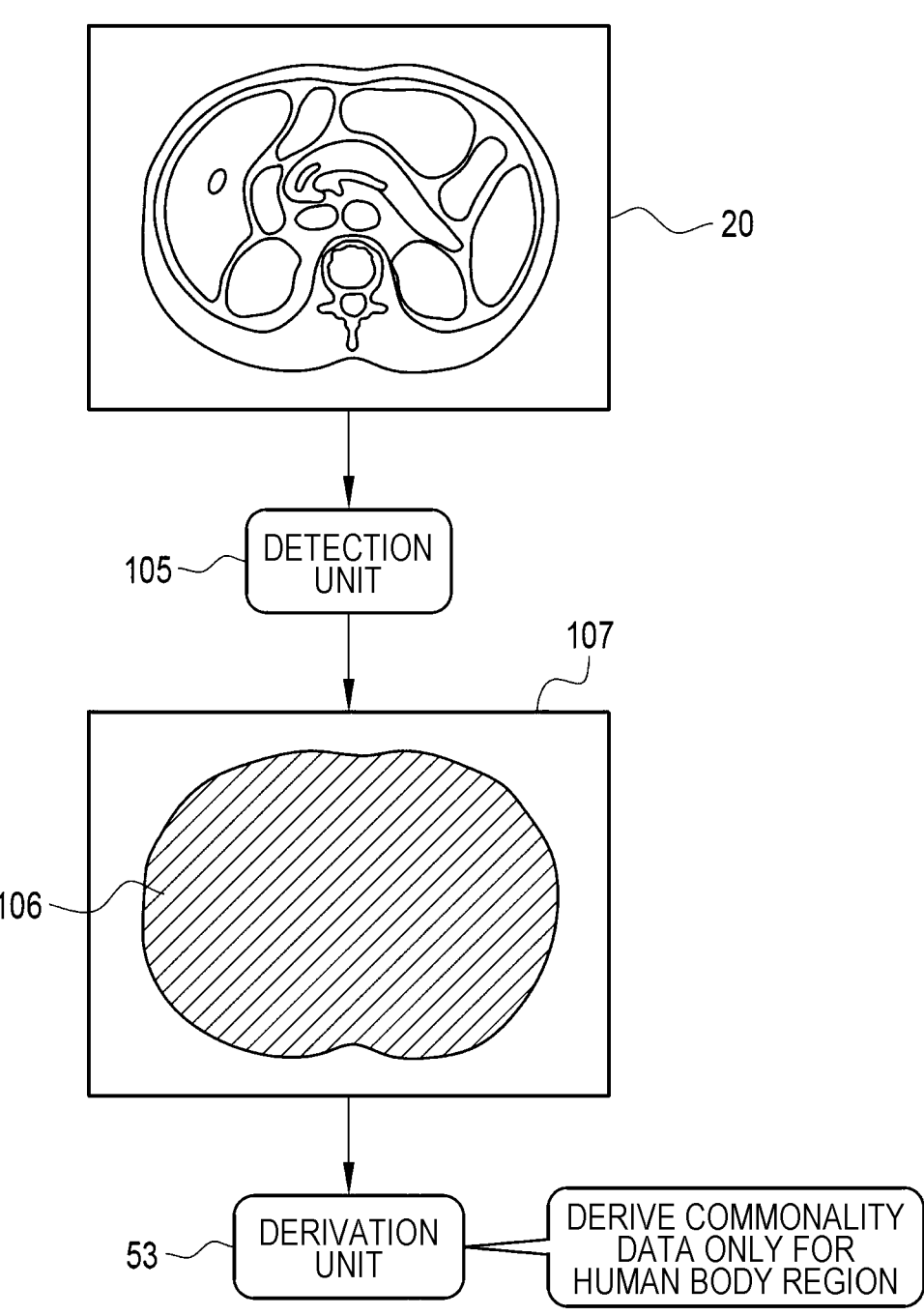
FIG. 14 is a diagram illustrating a fifth embodiment in which a human body region in which a human body appears in a medical image is detected and commonality data is derived only for the detected human body region.

As an example, as illustrated in FIG. 14, a processor of the support server of the present embodiment functions as a detection unit 105 in addition to each of the processing units 50 to 54 (units other than the derivation unit 53 are not illustrated) of the first embodiment. The detection unit 105 detects a human body region 106 in which a human body appears in the medical image 20 using a body surface recognition technique. The detection unit 105 outputs human body region information 107, which is a detection result of the human body region 106, to the derivation unit 53. Specifically, the human body region information 107 is position coordinates of a pixel of the medical image 20 corresponding to the human body region 106. The derivation unit 53 of the present embodiment derives the commonality data 60 only for the human body region 106.

As can be seen from the liver, the tumor, and the bleeding in the example, since the classes of the medical image 20 are set only for the human body region 106, it is not necessary to derive the commonality data 60 originally in a region other than the human body region 106. Therefore, in the fifth embodiment, the detection unit 105 detects the human body region 106 in which the human body appears in the medical image 20, and the derivation unit 53 derives the commonality data 60 only for the detected human body region 106. Therefore, a processing load of the derivation unit 53 can be reduced, and as a result, the generation of the confirmed annotation information 42 can be accelerated. Note that the commonality data 75 of the third_2 embodiment may be used instead of the commonality data 60.

Figure 15:
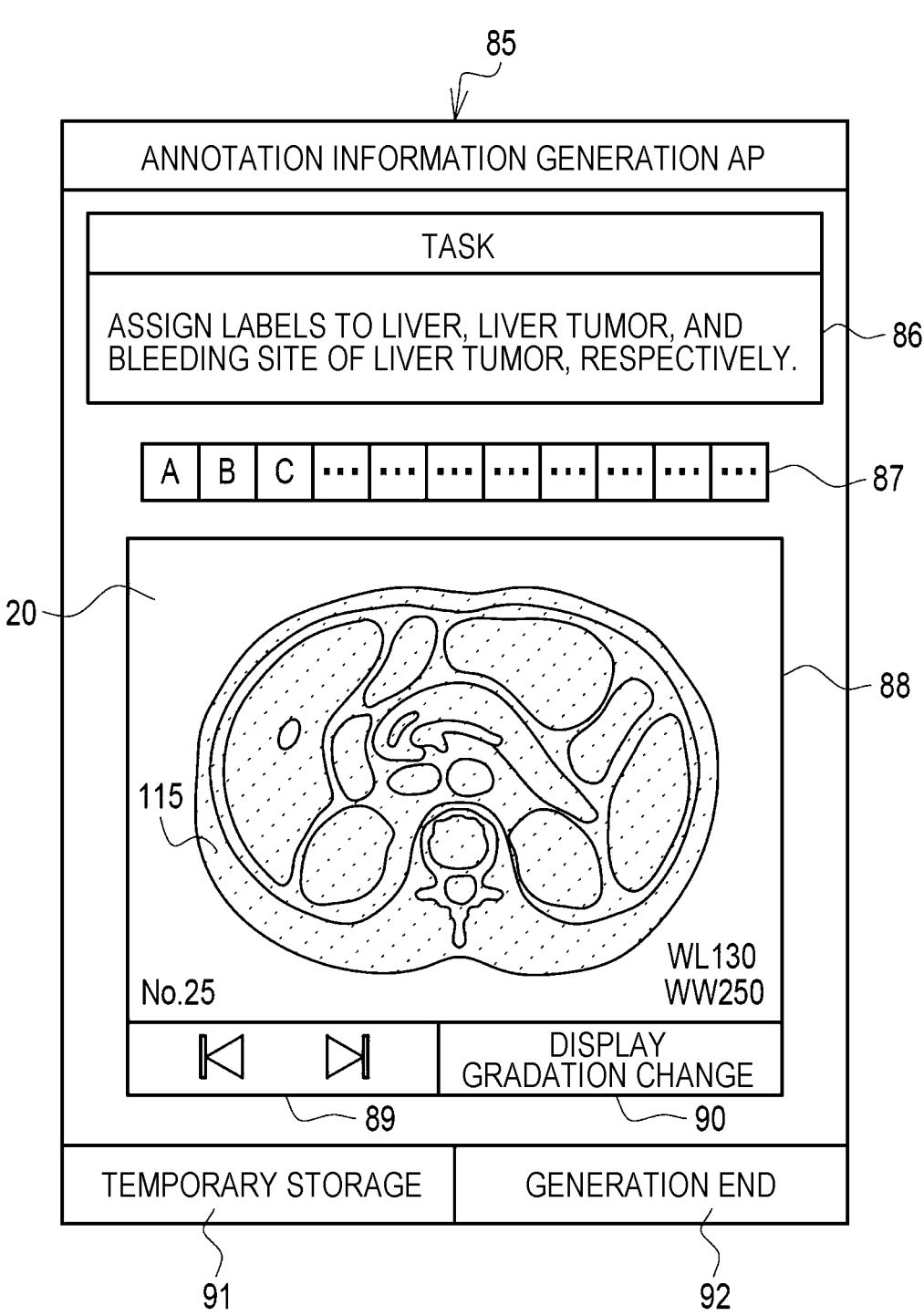
FIG. 15 is a diagram illustrating an annotation information generation screen on which a hatching pattern is displayed in a human body region.

As an example, as illustrated in FIG. 15, on the annotation information generation screen displayed on the display 13 of the annotator terminal 11, the human body region 106 detected by the detection unit 105 may be displayed with color half-tone dot meshing 115 indicated by hatching so as to be distinguishable from other regions. In this case, it is possible to alert of the annotator 15 so as not to erroneously assign a label to a region other than the human body region 106.

Furthermore, the annotation information generation screen 85 may be configured such that a label cannot be assigned to a region other than the human body region 106.

Such a configuration also makes it possible to prevent a label from being erroneously assigned to a region other than the human body region 106.

Sixth Embodiment

As an example, as illustrated in FIG. 16, the derivation unit 53 of the present embodiment counts the number of annotators 15 in a case of deriving the commonality data 60, according to annotator information 120. In the annotator information 120, for each annotator identification data (ID) for identifying each annotator 15, an attribute of the annotator 15 and the number of persons counted in a case where the commonality data 60 is derived are registered.

The attributes include the number of years of service and qualifications. The qualifications include radiology training instructors, radiological diagnosis specialists, and the like. The count number is determined according to a preset rule such that +0.5 is set in a case where the number of years of service is 20 years or more, −0.5 is set in a case where the number of years of service is less than 5 years, and +0.5 is set for qualified personnel. For example, since the annotator 15 with the annotator ID "AN0001" has the qualification of the radiology training instructor with the number of years of service of 22 years, the count number is 1+0.5+0.5=2. On the other hand, the annotator 15 with the annotator ID "AN0101" is not qualified because the number of years of service is three years. Therefore, the count number is 1-0.5=0.5.

As described above, in the sixth embodiment, in a case where the commonality data 60 is derived, weighting according to the attribute of the annotator 15 is performed. For this reason, it is possible to increase the number of persons counted in the region to which the labels have assigned by the annotators 15 considered to have relatively high accuracy of label assignment, such as the annotator 15 having a relatively long number of years of service and/or the annotator 15 of the qualified person. In this way, as in the confirmation condition 70 of the above described third_1 embodiment, in a case where the confirmation condition is that the label of the region in which the numerical value of the commonality data 60 is greater than or equal to the threshold value is adopted, the probability increases that the label assigned by the annotator 15 considered to have relatively high in accuracy of label assignment is adopted as the label of the confirmed annotation information 42. As a result, the reliability of the confirmed annotation information 42 can be increased.

Note that the commonality data 75 of the third_2 embodiment may be used instead of the commonality data 60. Also in this case, since the ratio of the region to which the label is assigned by the annotator 15 who is considered to have relatively high accuracy in label assignment becomes relatively high, the probability that the label assigned by the annotator 15 who is considered to have relatively high accuracy in label assignment is adopted as the label of the confirmed annotation information 42 increases, and as a result, the reliability of the confirmed annotation information 42 can be increased.

For example, in a case where there are an even number of annotators 15, and an equal number of annotators 15 have assigned and not assigned the labels, a method of assigning labels of a side to which the annotators 15 considered to have a relatively high accuracy in label assignment belongs may be adopted. Specifically, in a case where there are four annotators 15, there are two annotators 15 who have assigned the labels and two annotators 15 who have not assigned the labels, and the annotator 15 for which the accuracy in label assignment is considered to be relatively high is located on a side where the annotators who have not assigned the labels, the labels are not adopted as a label of the confirmed annotation information 42.

A specialized field of the annotator 15 may be included in the attribute. In this case, for example, in a case where the task has the content related to the specialized field, the count number is increased. Furthermore, the number of published papers by the annotator 15 may be included in the attribute. In this case, the count number is increased in a case where the number of published papers is greater than or equal to a first threshold value, and the count number is decreased in a case where the number of published papers is less than a second threshold value.

Seventh Embodiment

Figure 17:
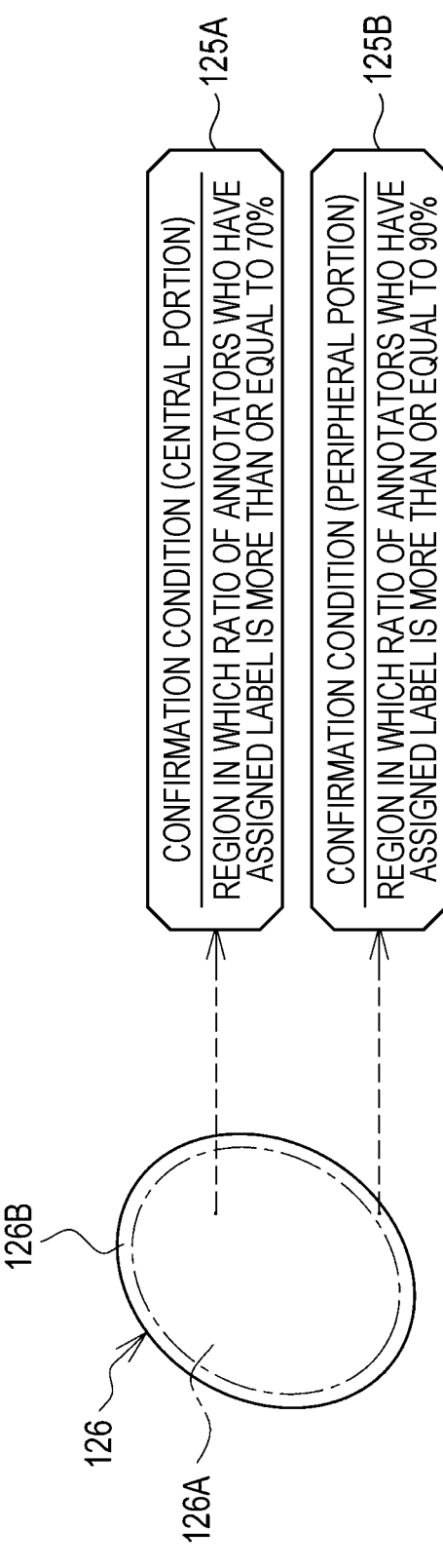
FIG. 17 is a diagram illustrating a seventh embodiment in which different confirmation conditions are set for a central portion and a peripheral portion of a region of a class.

For example, as illustrated in FIG. 17, the generation unit 54 (not illustrated) of the present embodiment generates the confirmed annotation information 42 based on two confirmation conditions 125A and 125B. The confirmation condition 125A is applied to a central portion 126A of a region 126 of the class. On the other hand, the confirmation condition 125B is applied to a peripheral portion 126B of the region 126. The content of the confirmation condition 125A is that a label of the region in which a ratio of the annotators 15 who have assigned the labels is more than or equal to 70% is adopted. On the other hand, the confirmation condition 125B is that a label of the region in which a ratio of the annotators 15 who have assigned the labels is more than or equal to 90% is adopted. Note that "70%" of the confirmation condition 125A and "90%" of the confirmation condition 125B are examples of a "threshold value" according to the technique of the present disclosure. That is, the threshold value of the confirmation condition 125B applied to the peripheral portion 126B is set to be higher than the threshold value of the confirmation condition 125A applied to the central portion 126A.

The central portion 126A and the peripheral portion 126B are selected, for example, as follows. First, a region to which the labels have been assigned by all the annotators 15 is obtained, and a center of the obtained region is set as a center of the central portion 126A. Note that the center is, for example, at least one of a center of gravity, an inner center, an outer center, or a vertical center. Next, the region to which the labels are assigned by all the annotators 15 is enlarged by, for example, 20% without moving the center. Then, the region to which the labels have been assigned by all the annotators 15 is set as the central portion 126A, and a region bordered by the region enlarged by 20% and the region to which the labels have been assigned by all the annotators 15 is set as the peripheral portion 126B. Alternatively, a center of each region to which the label is assigned by each annotator 15 may be obtained, a center of each obtained center may be obtained, and the obtained center may be used as a center of the central portion 126A. Note that a region obtained by enlarging the region to which the label is assigned by 20% without moving the center is set as the peripheral portion, but the present disclosure is not limited thereto. For example, in a case where a distance from the center of the region to which the labels have been assigned to an outer edge is set to 100, the distance from the center to 80 may be designated as the central portion, and the remaining distance from 80 to 100 may be designated as the peripheral portion.

As described above, in the seventh embodiment, the confirmation condition 125A applied to the central portion 126A of the region 126 of the class and the confirmation condition 125B applied to the peripheral portion 126B are provided, and the confirmation conditions are different between the central portion 126A and the peripheral portion 126B. The confirmation condition 125B has a higher difficulty level of satisfying the condition than the confirmation condition 125A. Since the peripheral portion 126B is a boundary with another region, it is particularly prone to incorrect labeling. Therefore, it is possible to ensure the reliability of the confirmed annotation information 42 in the peripheral portion 126B by setting the difficulty level of satisfying the condition to be higher in the peripheral portion 126B than in the central portion 126A.

Eighth Embodiment

Figure 18:
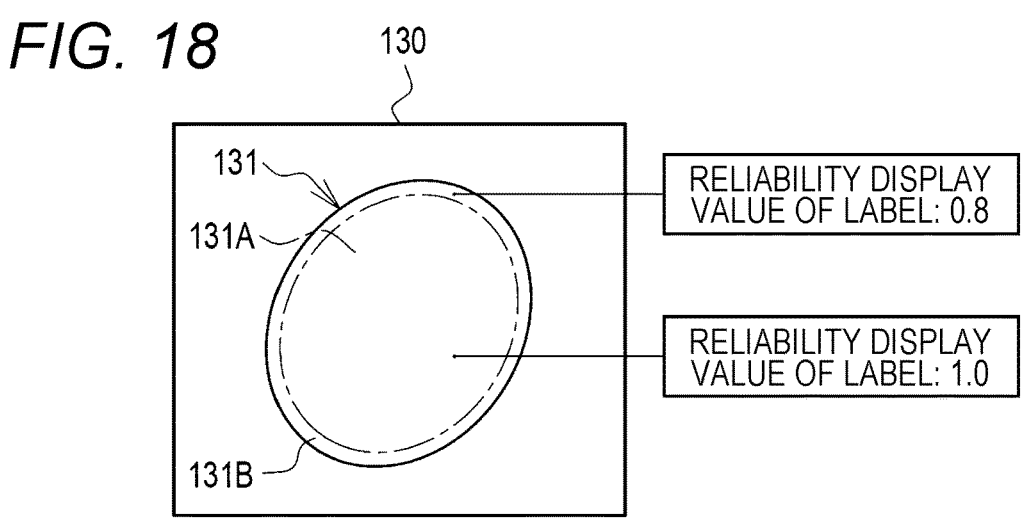
FIG. 18 is a diagram illustrating an eighth embodiment in which a reliability display value of a label of the peripheral portion is set to be lower than that of the central portion of the region of the class in the confirmed annotation information.

As an example, as illustrated in FIG. 18, the generation unit 54 (not illustrated) according to the present embodiment sets a numerical value (hereinafter, referred to as a reliability display value) representing the reliability of the label of a peripheral portion 131B to be lower than that of a central portion 131A of a region 131 of the class in confirmed annotation information 130. To be specific, the generation unit 54 sets the reliability display value of the central portion 131A to the maximum value of 1, and sets the reliability display value of the peripheral portion 131B to 0.8. Note that the central portion 131A and the peripheral portion 131B are also selected as in the central portion 126A and the peripheral portion 126B of the seventh embodiment.

As described above, in the eighth embodiment, the generation unit 54 sets the reliability display value of the label to be lower in the peripheral portion 131B than in the central portion 131A of the region 131 of the class in the confirmed annotation information 130. Therefore, in a case where a machine learning model is trained using the confirmed annotation information 130, it is possible to reduce a frequency of occurrence of so-called false positive in which a region that is not a class is recognized as a class, especially in an initial stage of the learning phase.

The reliability display value of the label in the confirmed annotation information may be set according to the ratio of the annotators 15 who have assigned the labels, which has been described in the third_2 embodiment. For example, the ratio of the annotators 15 who have assigned the labels is used as the reliability display value as it is. Specifically, the reliability display value is set to 0.8 in a case where the ratio is 80%, and the reliability display value is set to 0.2 in a case where the ratio is 20%.

Figure 19:
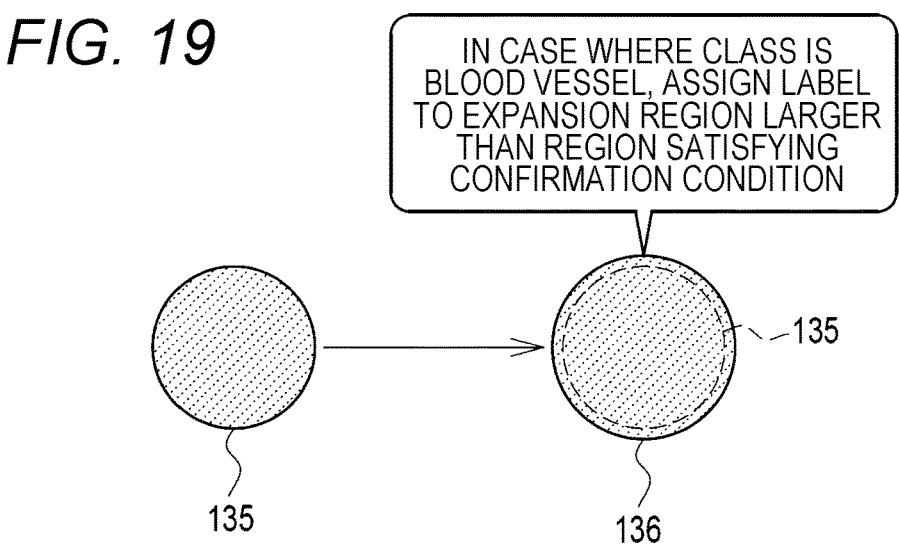
FIG. 19 is a diagram illustrating a method of assigning a label in a case where a class is a blood vessel.

Note that, for example, as illustrated in FIG. 19, in a case where the class is a blood vessel, it is preferable that the generation unit 54 assigns a label to an expansion region 136 that is larger than the region 135 satisfying the confirmation condition in the confirmed annotation information. The expansion region 136 is, for example, a region that is larger than the region 135 satisfying the confirmation condition by the number of set pixels. The number of set pixels is, for example, one. In the case of the blood vessel, since the boundary is often unclear, there is a demand for recognizing the periphery of the blood vessel as a blood vessel with a margin, and thus, the demand can be met. Note that the expansion region 136 may be a region including a distance from an outer edge to, for example, 120 in a case where a distance from the center of the region 135 satisfying the confirmation condition to the outer edge is 100. The center of the region 135 that satisfies the confirmation condition may be obtained in the same manner as the center of the region to which the labels are assigned by all the annotators 15 in the seventh embodiment.

Ninth Embodiment

Figure 20:
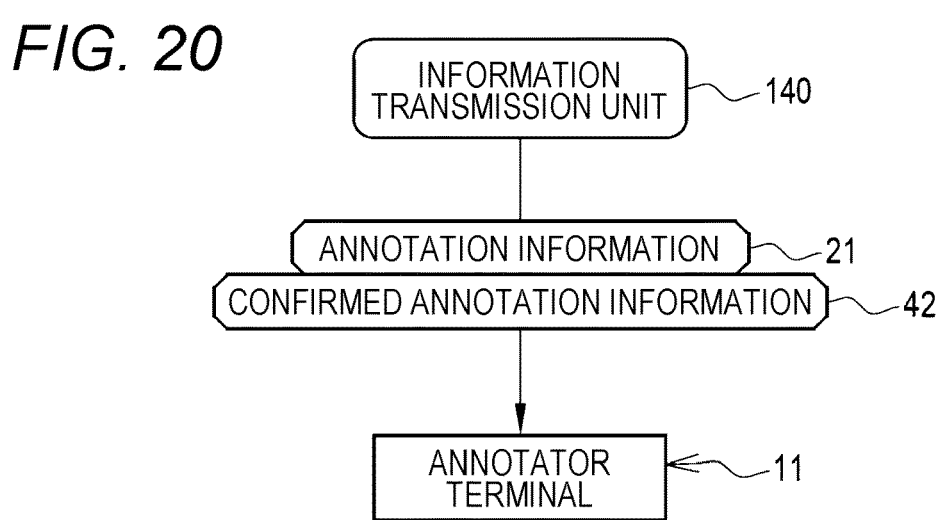
FIG. 20 is a diagram illustrating a ninth embodiment in which annotation information and confirmed annotation information are transmitted to an annotator terminal.

As an example, as illustrated in FIG. 20, a processor of the support server of the present embodiment functions as an information transmission unit 140 in addition to each of the processing units 50 to 54 of the first embodiment. The information transmission unit 140 transmits the annotation information 21 and the confirmed annotation information 42 stored in the storage 30 to the annotator terminal 11. The annotation information 21 may include not only information generated by the annotator 15 of the annotator terminal 11 that is a transmission destination but also information generated by an annotator other than the annotator 15 of the annotator terminal 11 that is a transmission destination.

Figure 21:
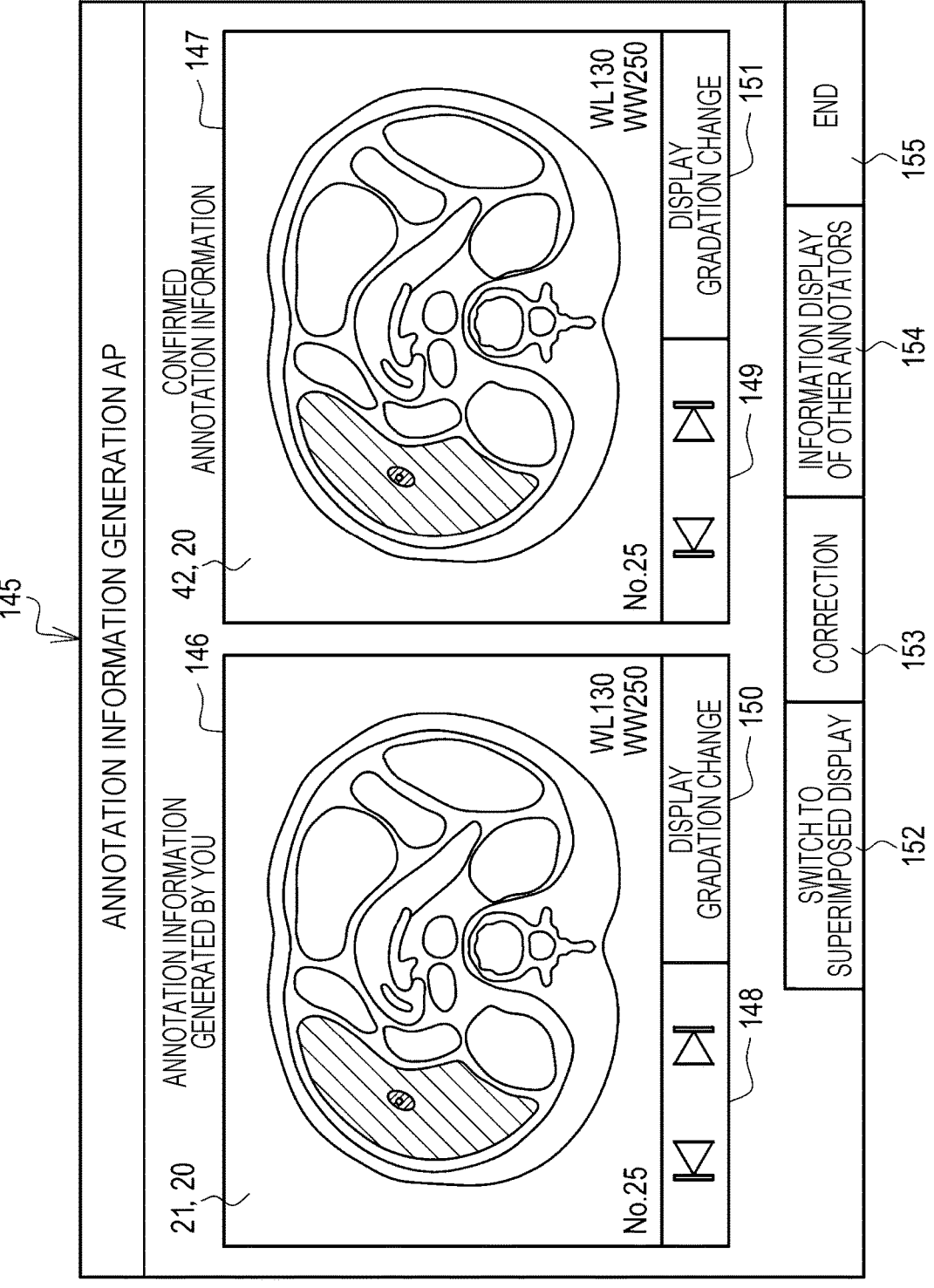
FIG. 21 is a diagram illustrating an information comparison screen displayed on a display of the annotator terminal.

In the annotator terminal 11 that has received the annotation information 21 and the confirmed annotation information 42, an information comparison screen 145 illustrated in FIG. 21 is displayed on the display 13 as an example. The information comparison screen 145 includes an annotation information display region 146 in which the annotation information 21 is superimposed and displayed on the medical image 20, and a confirmed annotation information display region 147 in which the confirmed annotation information 42 is superimposed and displayed on the medical image 20. The annotation information display region 146 and the confirmed annotation information display region 147 are arranged side by side on the left and right.

First, the annotation information 21 generated by the annotator 15 is displayed in the annotation information display region 146. Furthermore, the medical image 20 superimposed on the annotation information 21 and the medical image 20 superimposed on the confirmed annotation information 42 are initially displayed under the same display condition according to the display condition data 81.

FIG. 21 illustrates an example in which the regions to which all the labels of the liver, the tumor, and the bleeding are assigned are displayed, but the annotation information 21 and the confirmed annotation information 42 may be displayed for each class such as only the region to which the label of the liver is assigned.

Feedback buttons 148 and 149 and display gradation change buttons 150 and 151, which have the same functions as the feedback button 89 and the display gradation change button 90 of the annotation information generation screen 85, are provided in a lower portion of the annotation information display region 146 and the confirmed annotation information display region 147. Therefore, similarly to the case of the annotation information generation screen 85, the slice position can be changed, and the window level and the window width can be changed.

In the lower portion of the information comparison screen 145, a display mode switch button 152, a correction button 153, an information switch button 154, and an end button 155 are further provided. In a case where the display mode switch button 152 is operated, the annotation information 21 in the annotation information display region 146 is moved to the confirmed annotation information display region 147, and the annotation information 21 and the confirmed annotation information 42 are displayed in a superimposed manner. In this case, a part where the label of the annotation information 21 overlaps with the label of the confirmed annotation information 42 is displayed in a darker color than a part where the labels do not overlap. In a case where the correction button 153 is operated, the screen changes to the annotation information generation screen 85, and the annotation information 21 can be corrected. In a case where the information switch button 154 is operated, the display of the annotation information display region 146 is switched from the annotation information 21 generated by the annotator 15 to the annotation information 21 generated by another annotator 15. In a case where the end button 155 is operated, the display of the information comparison screen 145 is cleared.

As described above, in the ninth embodiment, the information transmission unit 140 transmits the annotation information 21 and the confirmed annotation information 42 to the annotator terminal 11 operated by the annotator 15. Therefore, as illustrated in FIG. 21, it is possible to display the annotation information 21 and the confirmed annotation information 42 to the annotator 15 in a comparable manner. The annotator 15 compares the annotation information 21 generated by the annotator 15 itself with the confirmed annotation information 42 and uses the compared information to generate the annotation information 21 in the future. Furthermore, in some cases, the annotation information 21 can be corrected with reference to the confirmed annotation information 42.

Note that the display condition of the medical image 20 superimposed on the annotation information 21 and the display condition of the medical image 20 superimposed on the confirmed annotation information 42 may be set as a display condition that has been set that most number of times among the display conditions set by each annotator 15 on the annotation information generation screen 85. Furthermore, the following may be performed. That is, the support server 10 receives the window level and the window width at the time of ending the generation of the annotation information 21 from each annotator terminal 11 together with the annotation information 21. The support server 10 sets the window level and the window width attached to the annotation information 21 approximate to the confirmed annotation information 42 among the received window levels and window widths as the display conditions of the medical image 20 superimposed on the annotation information 21 and the medical image 20 superimposed on the confirmed annotation information 42.

In the first embodiment, the medical image 20 is transmitted from the support server 10 to the annotator terminal 11, but the present disclosure is not limited thereto. For example, an image management server that accumulates and manages the medical image 20 may be provided separately from the support server 10, and the medical image 20 may be transmitted from the image management server to the annotator terminal 11.

The medical image 20 is not limited to the abdominal tomographic image captured by the exemplary CT apparatus. For example, a head tomographic image captured by a magnetic resonance imaging (MM) apparatus may be used. Furthermore, the medical image is not limited to a three-dimensional image such as a tomographic image. For example, a two-dimensional image such as a simple radiographic image may be used. The medical image may be a positron emission tomography (PET) image, a single photon emission computed tomography (SPECT) image, an endoscopic image, an ultrasound image, a funduscopy image, and the like.

The class to which the label is assigned is also not limited to the exemplified liver, tumor, bleeding, and blood vessel. The anatomical regions may include other organs such as a brain, eyes, a spleen, and a kidney, as well as bones such as the vertebrae and the ribs, anatomical regions of organs such as S1 to S10 segments of the a lung, the pancreatic head, pancreatic body, and the pancreas tail of the pancreas, and other abnormal finding regions such as the cyst, atrophy, stenosis of the duct, or dilation of the duct. Furthermore, a pacemaker, an artificial joint, a bolt for fracture treatment, and the like may be used.

A value adapted to the type of the medical image 20, an organ as a class, the body type of the patient, or the like is set as the display condition data 81 of the fourth embodiment. In a case where the medical image 20 is a radiographic image, a value adapted to an amount of irradiated radiation is further set as the display condition data 81.

The label is assigned in units of pixels of the medical image 20, but the present disclosure is not limited thereto. For example, a label may be assigned to a rectangular frame (in a case where the medical image 20 is a two-dimensional image) or box-shaped frame (in a case where the medical image 20 is a three-dimensional image) surrounding the entire class such as a tumor. In this case, for example, the label assigned to the region where all the frames overlap is adopted as the label of the confirmed annotation information 42.

In each of the embodiments described above, the annotator 15 is described as a person such as a doctor, but is not limited thereto. The annotator 15 may be a machine learning model.

Various screens such as the annotation information generation screen 85 may be transmitted from the support server 10 to the annotator terminal 11 in a format of screen data for web distribution created by a markup language such as Extensible Markup Language (XML). In this case, the annotator terminal 11 reproduces various screens to be displayed on a web browser based on the screen data and displays the various screens on the display 13. Note that, instead of XML, another data description language such as JavaScript (registered trademark) Object Notation (JSON) may be used.

Various modifications are possible for a hardware configuration of the computer constituting the support server 10. For example, the support server 10 may be configured by a plurality of server computers separated as hardware for the purpose of improving processing capability and reliability. For example, the functions of the RW control unit 50, the image transmission unit 51, and the information reception unit 52, and the functions of the derivation unit 53 and the generation unit 54 may be distributed to two server computers. In this case, the support server 10 is configured by two server computers. The annotator terminal 11 may assume some or all of the functions of the respective processing units of the support server 10.

As described above, the hardware configuration of the computer of the support server 10 can be appropriately changed according to required performance such as processing capability, safety, and reliability. Moreover, it is needless to say that not only the hardware but also the AP such as the operation program 40 can be duplicated or distributed and stored in a plurality of storages for a purpose of ensuring safety and reliability.

In each of the above-described embodiments, for example, the following various processors can be used as a hardware structure of processing units performing various processes, such as the RW control unit 50, the image transmission units 51 and 80, the information reception unit 52, the derivation unit 53, the generation unit 54, the detection unit 105, and the information transmission unit 140. The various processors include a CPU that is a generalpurpose processor executing software (the operation program 40) to function as various processing units, a programmable logic device (PLD) that is a processor capable of changing a circuit configuration after manufacture, such as a field-programmable gate array (FPGA), and/or a dedicated electric circuit that is a processor having a circuit configuration exclusively designed to execute specific processing, such as an application-specific integrated circuit (ASIC).

One processing unit may be configured by one of these various processors, or may be configured by a combination of two or more processors of the same type or different types (for example, a combination of a plurality of FPGAs and/or a combination of a CPU and an FPGA). Furthermore, the plurality of processing units may be configured by one processor.

As an example in which the plurality of processing units are configured by one processor, first, as represented by a computer such as a client and a server, there is a form in which one processor is configured by a combination of one or more CPUs and software and this processor functions as the plurality of processing units. Second, as represented by a system-on-chip (SoC) or the like, there is a form in which a processor that realizes the functions of the entire system including a plurality of processing units with one integrated circuit (IC) chip is used. As described above, the various processing units are configured using one or more of the various processors as a hardware structure.

More specifically, an electric circuit (circuitry) in which circuit elements such as semiconductor elements are combined can be used as the hardware structure of the various processors.

[Supplementary Note 1]

It is preferable that the annotation information is information in which the labels of the classes different from each other are assigned to the same region.

[Supplementary Note 2]

It is preferable that the commonality data is a numerical value related to the number of persons of the annotators who have assigned the labels for each of the plurality of classes, and the confirmation condition is that the assigned labels are adopted only in a case where the numerical value is more than or equal to a threshold value.

[Supplementary Note 3]

It is preferable for display condition data to be attached to the medical image in a case where the plurality of annotators view the medical image, in order to display the medical image under the same display conditions.

[Supplementary Note 4]

It is preferable that the processor detects a human body region in which a human body appears in the medical image, and derives the commonality data only for the detected human body region.

[Supplementary Note 5]

It is preferable that the processor performs weighting according to an attribute of the annotators in a case where deriving the commonality data.

[Supplementary Note 6]

It is preferable that the confirmation condition is different between a central portion and a peripheral portion of the region of the classes, and a difficulty level of satisfying the condition is higher in the peripheral portion than in the central portion.

[Supplementary Note 7]

It is preferable that the processor sets a numerical value representing reliability of the labels at a peripheral portion to be lower than a numerical value representing reliability of the labels at a central portion of the region of the classes in the confirmed annotation information.

[Supplementary Note 8]

It is preferable that the processor transmits the annotation information and the confirmed annotation information to annotator terminals used by the annotators.

In the technique of the present disclosure, the above-described various embodiments and/or various modification examples can be appropriately combined. Furthermore, it is needless to say that the present disclosure is not limited to each of the above-described embodiments and various configurations can be adopted without departing from the scope of the present disclosure. Moreover, the technique of the present disclosure extends to a storage medium that non-transitorily stores a program in addition to the program.

The contents described and illustrated above are detailed descriptions of portions according to the technique of the present disclosure and are merely examples of the technique of the present disclosure. For example, the above description of the configurations, functions, actions, and effects is an example of the configurations, functions, actions, and effects of the portions according to the technique of the present disclosure. Accordingly, it goes without saying that unnecessary portions may be deleted, new elements may be added, or replacement may be made with respect to the described contents and the illustrated contents described above without departing from the scope of the technique of the present disclosure. Furthermore, in order to avoid confusion and to facilitate understanding of portions according to the technique of the present disclosure, description related to common technical knowledge or the like that does not needs to be particularly described for enabling implementation of the technique of the present disclosure is omitted in the description contents and the illustration contents described above.

In the present specification, "A and/or B" has the same meaning as "at least one of A or B". That is, "A and/or B" means that only A may be used, only B may be used, or a combination of A and B may be used. Furthermore, in the present specification, in a case where three or more matters are expressed by being connected by "and/or", the same concept as "A and/or B" is applied.

All documents, patent applications, and technical standards described in this specification are herein incorporated by reference to the same extent as if each individual publication, patent application, or technical standard was specifically and individually indicated to be incorporated by reference.

What is claimed is:

1. A machine learning model creation support apparatus comprising a processor, wherein the processor acquires a plurality of pieces of annotation information generated by a plurality of annotators assigning a plurality of labels according to a plurality of classes to a region of the same medical image, derives, for each of the classes, commonality data indicating commonality of the labels are assigned to the region of the same medical image by the plurality of annotators for the plurality of pieces of annotation information, and generates confirmed annotation information used as correct answer data of a machine learning model based on the commonality data and a preset confirmation condition.

2. The machine learning model creation support apparatus according to claim 1, wherein the annotation information is information in which the labels of the classes different from each other are assigned to the same region.

3. The machine learning model creation support apparatus according to claim 1, wherein:

the commonality data is a numerical value related to the number of persons of the annotators who have assigned the labels for each of the plurality of classes, and the confirmation condition is that the assigned labels are adopted only in a case where the numerical value is more than or equal to a threshold value.

4. The machine learning model creation support apparatus according to claim 1, wherein display condition data for displaying the medical image under the same display condition in a case where the plurality of annotators view the medical image is attached to the medical image.

5. The machine learning model creation support apparatus according to claim 1, wherein the processor detects a human body region in which a human body appears in the medical image, and derives the commonality data only for the detected human body region.

6. The machine learning model creation support apparatus according to claim 1, wherein the processor performs weighting according to an attribute of the annotators in a case of deriving the commonality data.

7. The machine learning model creation support apparatus according to claim 1, wherein the confirmation condition is different between a central portion and a peripheral portion of the region of the classes, and a difficulty level of satisfying the condition is higher in the peripheral portion than in the central portion.

8. The machine learning model creation support apparatus according to claim 1, wherein the processor sets a numerical value representing reliability of the labels at a peripheral portion to be lower than a numerical value representing reliability of the labels at a central portion of the region of the classes in the confirmed annotation information.

9. The machine learning model creation support apparatus according to claim 1, wherein the processor transmits the annotation information and the confirmed annotation information to annotator terminals used by the annotators.

10. A method of operating a machine learning model creation support apparatus, the method comprising:

acquiring a plurality of pieces of annotation information generated by a plurality of annotators assigning a plurality of labels according to a plurality of classes to a region of the same medical image;

deriving, for each of the classes, commonality data indicating commonality of the labels are assigned to the region of the same medical image by the plurality of annotators for the plurality of pieces of annotation information; and generating confirmed annotation information used as correct answer data of a machine learning model based on the commonality data and a preset confirmation condition.

11. A non-transitory computer-readable storage medium storing a program for operating a machine learning model creation support apparatus, the program causing a computer to execute processing of:

acquiring a plurality of pieces of annotation information generated by a plurality of annotators assigning a plurality of labels according to a plurality of classes to a region of the same medical image;

deriving, for each of the classes, commonality data indicating commonality of the labels are assigned to the region of the same medical image by the plurality of annotators for the plurality of pieces of annotation information; and generating confirmed annotation information used as correct answer data of a machine learning model based on the commonality data and a preset confirmation condition.

\* \* \* \* \*